United States Patent [19]

Yamano et al.

[11] Patent Number: 5,043,276

[45] Date of Patent: Aug. 27, 1991

[54] DNA STRAND CODING FOR ALPHA-ACETOLACTATE DECARBOXYLASE AND YEAST TRANSFORMED WITH THE DNA STRAND

[75] Inventors: Shigeyuki Yamano; Junichi Tanaka, both of Takasaki; Takashi Inoue, Tokyo, all of Japan

[73] Assignee: Kirin Beer Kabushiki Kaisha, Tokyo, Japan

[21] Appl. No.: 341,379

[22] Filed: Apr. 20, 1989

[30] Foreign Application Priority Data

Apr. 22, 1988 [JP] Japan .................................. 63-100061
Dec. 27, 1988 [JP] Japan .................................. 63-330335
Apr. 19, 1989 [JP] Japan .................................. 64-99685

[51] Int. Cl.⁵ .......................... C12P 21/00; C12C 1/00; C12G 1/00; C07H 15/12
[52] U.S. Cl. ................................ 435/161; 432/320.1; 432/91; 432/255; 432/256; 432/232; 432/172.3; 536/27; 426/11; 426/12; 935/56; 935/69
[58] Field of Search ............... 536/27; 435/172.3, 232, 435/320, 940, 254, 255, 256, 320.1, 161; 426/11.12; 935/56, 69

[56] References Cited

U.S. PATENT DOCUMENTS 4,617,273 10/1926 Olsen .................................. 435/172.5
4,895,802  1/1980 Sone et al. ........................ 433/172.5

FOREIGN PATENT DOCUMENTS 0128714 12/1984 European Pat. Off. .
0163491 12/1985 European Pat. Off. .
0228009  7/1987 European Pat. Off. .

OTHER PUBLICATIONS

"Cloning and Expression-" Goelling et al.; Applied and Environmental Microbiology 1889-1891 (1988).
"Molecular Cloning-" H. Sone; Journal of Biotechnology vol. 5, 1987.
Article "Acetolactate Decarboxylase from Aerobacter . . . " Loken et al.; Eur. J. Biochem. 14, 1970, 133-137;
Article 2,3-Butanediol Biosynthetic-Stromer; Methods in Enzymology, vol. 41, pp. 518-533.
Article "Use of A-Acetolactate-" Godtfredsen et al. Proceedings of the European Brewery Convention, 1986 pp. 161-168
Carlsberg Res. Commun., vol. 48, 1983, pp. 239-247; S. E. Godtfredsen: "On the Occurrence of Alpha-Acetolactate Decarboxylases Among Microorganisms".
EBC Congress 1983, vol. 89, lecture No. 17, pp. 161-168; S. E. Godtfredsen et al.: "Use of Alpha-Acetolactate Decarboxylase for Accelerated Maturation of Beer".

*Primary Examiner*—Robin L. Teskin
*Attorney, Agent, or Firm*—Ladas & Parry

[57] ABSTRACT

DNA strand having an ability in biotechnological production of α-acetolactate decarboxylase is disclosed. The DNA strand is characterized in that it has a nucleotide sequence coding for a polypeptide whose amino acid sequence is substantially from A to B of FIG. 1 and which has α-acetolactate decarboxylase activity. Also disclosed is a yeast which belongs a *Saccharomyces cerevisiae* and which has been transformed by the DNA strand. The yeast is characterized by the fact that its α-acetolactate producing ability is reduced, and will thus produce an alcoholic liquor such as beer which contains no or little diacetyls which have come from their precursor, namely α-acetolactate.

20 Claims, 15 Drawing Sheets

```
      G GTA CCG GGA CCA TAG GGG GGC TTG GGG TCG CTT TCG GCA TGG GCG       46

47  CGC TGC TGC CCG CGA TCA GGC CGC CCA TGC AGA AGG CGG CGA GCG TCA       94

95  TGT AAA GTG GCT TCA TAT CCG GTC ATC CTG AAT TTC AAT GCG CGT TCA      142

143  CAA TGG CAG TCC TGA ACG GCC AAG GGC AAG GCC AGG GCC TGC ACG GCG      190

191  GCA TTT CCA TAT ATT TTA TAT ATG GAA ATA GGC TTT AAT ATA TAT TGG      238
                                  Met¹Glu Ile Gly Phe Asn Ile Tyr Trp       9
                                   ᴸA1
 239  ACG TAC GAA CCT GCC TGC ATC ACC ATT AGT CTG CAA TCA CAA ATG ACC      286
  10  Thr Tyr Glu Pro Ala Cys Ile Thr Ile Ser Leu Gln Ser Gln Met²Thr       25
                                                              ᴸA2
 287  GGG TTG AGG CGA TGC CAT GTG CCG CAT TGT CCC CCG ATG CAG GAG ACT      334
  26  Gly Leu Arg Arg Cys His Val³Pro His Cys Pro Pro Met⁴Gln Glu Thr       41
                            ᴸA3                     ᴸA4
 335  GAG GTC GTG AAG CTT AAA TGC TAC TCG GTA GGG GAT GTT GAT ACC CGG      382
  42  Glu Val Val⁵Lys Leu Lys Cys Tyr Ser Val Gly Asp Val Asp Thr Arg       57
              ᴸA5
 383  TCC AGC GCT GCT GAT TCG ACT GGC GTG CGT CCG CGC ATG AAC CGC CTG      430
  58  Ser Ser Ala Ala Asp Ser Thr Gly Val⁶Arg Pro Arg Met⁷Asn Arg Leu       73
                       NcoI              ᴸA6        ᴸA7
 431  TAC CAG ACA TCG ACC ATG GCC GCG CTG CTT GAT GCG GTC TAT GAT GGC      478
  74  Tyr Gln Thr Ser Thr Met Ala Ala Leu Leu Asp Ala Val Tyr Asp Gly       89

479  GAG ACC ACG CTT GAT GAA CTG CTG ATG CAC GGC AAT TTC GGG CTG GGC      526
  90  Glu Thr Thr Leu Asp Glu Leu Leu Met His Gly Asn Phe Gly Leu Gly      105

527  ACG TTC AAC GGC CTT GAT GGC GAG ATG ATC GTC AAT GAC AGC GTA ATC      574
 106  Thr Phe Asn Gly Leu Asp Gly Glu Met Ile Val Asn Asp Ser Val Ile      121

575  CAC CAG TTC CGT GCA GAC GGG CAG GCC GGT CGT GTG CCG GGC GAC CTC      622
 122  His Gln Phe Arg Ala Asp Gly Gln Ala Gly Arg Val Pro Gly Asp Leu      137

623  AGG ACT CCG TTC GCC TGC GTT ACC TTC TTC AAC CCG GAG AAG GAA TAC      670
 138  Arg Thr Pro Phe Ala Cys Val Thr Phe Phe Asn Pro Glu Lys Glu Tyr      153

671  ATG ATC GAC ACC GCG CAG GAT AAG GAA GGC TTC GAG GCG ATC GTG GAT      718
 154  Met Ile Asp Thr Ala Gln Asp Lys Glu Gly Phe Glu Ala Ile Val Asp      169

719  CAC CTC GTC AAC AAT CCC AAC CTG TTC GCC GCC GTG CGC TTT ACC GGC      766
 170  His Leu Val Asn Asn Pro Asn Leu Phe Ala Ala Val Arg Phe Thr Gly      185

767  ATG TTC GAG CGG GTC GAG ACC CGC ACC GTG TTC TGC CAG TGC CAG CCC      814
 186  Met Phe Glu Arg Val Glu Thr Arg Thr Val Phe Cys Gln Cys Gln Pro      201

815  TAC CCA CCC ATG CTG GAA GTG GTG GCC CGC CAG CCC ACC ATG CAG CTT      862
 202  Tyr Pro Pro Met Leu Glu Val Val Ala Arg Gln Pro Thr Met Gln Leu      217

863  GGT GCC TCC ACC GGC ACC ATG CTT GGT TTC CGC ACG CCG GGC TAC ATG      910
 218  Gly Ala Ser Thr Gly Thr Met Leu Gly Phe Arg Thr Pro Gly Tyr Met      233

911  CAG GGC GTG AAC GTG GCG GGT TAT CAC CTG CAC TTC CTG ACT GAG GAC      958
 234  Gln Gly Val Asn Val Ala Gly Tyr His Leu His Phe Leu Thr Glu Asp      249

959  GGA CGC CGT GGC GGC CAT GTG ACC GAT TAC GGC GTG CTG CGC GGT CGG     1006
 250  Gly Arg Arg Gly Gly His Val Thr Asp Tyr Gly Val Leu Arg Gly Arg      265

1007  CTT GAG GTG GGC GTG ATT TCC GAT GTG GAA ATC CAG CTG CCC CGC ACC     1054
 266  Leu Glu Val Gly Val Ile Ser Asp Val Glu Ile Gln Leu Pro Arg Thr      281

1055  GAA CAG TTC GCG CGC GCC AAC CTG TCC CCC GAA AAC ATT CAC GAG GCC     1102
 282  Glu Gln Phe Ala Arg Ala Asn Leu Ser Pro Glu Asn Ile His Glu Ala      297

1103  ATT CGC GTG GCC GAG GGC GGC TGA GGG TTT CCC CTC CCG CCT GAG CAA     1150
 298  Ile Arg Val Ala Glu Gly Gly
                              ᴸB
1151  CTG TCC GCT CCG CCC CGG CTG CGG TGC AAA CCG TTC AGG ATA CCT GAA     1198

1199  ATC ATG ACT GAC AAG ACC AAA TCG GCC GCG CCG GAG TGC GGG GCG GAC     1246

1247  ATG ATC
```

FIG.I

DNA STRAND CODING FOR ALPHA-ACETOLACTATE DECARBOXYLASE AND YEAST TRANSFORMED WITH THE DNA STRAND

BACKGROUND OF THE INVENTION

1. Field of the Art

This invention relates to a DNA strand having an ability in biotechnological production of α-acetolactate decarboxylase (hereinafter called α-ALDCase) as produced by *Acetobacter aceti* subspecies xylinum IFO 3288, to a yeast belonging to *Saccharomyces cerevisiae* transformed with the DNA strand so that it has capability of producing α-ALDCase, and to production of alcoholic beverages by the yeast transformed.

2. Prior art

Alcoholic beverages such as beer, sake, wine, etc., are generally produced by adding a yeast belonging to *Saccharomyces cerevisiae* to a starting material liquid for fermentation such as wort, fruit juice, etc., and subjecting the mixture to alcohol fermentation. In the fermentation process, the yeast will produce α-acetolactate (hereinafter called α-AL) as the intermediate substance for biosynthesis of valine and leucine which are amino acids necessary for the growth of itself, and leak it inevitably out of the cell, namely into the fermented liquor. The α-AL which has thus become to exist in the fermented liquor will change spontaneously to diacetyl (hereinafter called DA) through the non-enzymatical reaction in the fermented liquor.

DA is a substance having strong objectionable odor called generally as "cooked odor" or "DA odor" and, in order to produce an alcoholic beverage excellent in flavor (namely without DA odor), the content of α-AL and DA in the fermented liquor is required to be decreased to a low level so that the total DA content will not finally exceed the discrimination threshold of DA odor in the alcoholic beverage (e.g. 0.05 to 0.1 mg/liter in the case of beer) even if α-AL may be all changed to DA.

While DA in the fermented liquor is converted to acetoin which is tasteless and odorless relatively rapidly in the co-presence of yeast, α-AL in the fermented liquor will not be changed by yeast, but it becomes decomposable with yeast only after it has been changed to DA by non-enzymatical chemical reaction. However, since the conversion of α-AL to DA in the fermented liquor proceeds at a very slow rate, this reaction becomes the rate-limiting step, whereby the fermented liquor is required to be aged under the co-presence of yeast for a long time in order to obtain an alcoholic beverage with low content of α-AL and DA (namely without DA odor).

α-ALDCase is an enzyme having the property of converting α-AL to acetoin and has been known to be produced by various Voges Proskauer reaction positive bacteria such as *Enterobacter aerogenes, Bacillus licheniformis, Lactobacillus casei, Bacillus brevis, Enterobacter cloacae*, and *Acetobacter* bacteria (such as *A. rancens, A. aceti*, etc), etc.

SUMMARY OF THE INVENTION

The present invention provides a DNA strand having an ability in biotechnological production of α-ALDCase, which is useful for production of alcoholic beverages having no DA odor within by far shorter period as compared with the prior art method, and a yeast endowed with α-ALDCase producing ability by transformation with the DNA strand.

More specifically, the DNA sequence coding for α-ALDCase according to the present invention is characterized in that it has a nucleotide sequence, or, in other words, a nucleotide sequence coding for a polypeptides having α-ALDCase activity, of which amino acid sequence, namely an amino acid sequence of the polypeptides, is substantially from A to B of the amino acid sequence shown in FIG. 1.

On the other hand, the yeast belonging to *Saccharomyces cerevisiae* according to the present invention is characterized in that it is yeast which has been transformed with a DNA sequence coding for the polypeptides having α-ALDCase activity, of which amino acid sequence is substantially from A to B of the amino acid sequence shown in FIG. 1.

The present invention also relates to the use of the DNA sequence or strand and the yeast.

Accordingly, the process for producing an alcoholic beverage according to the present invention is characterized in that fermenting a material for fermentation by a yeast which is a yeast which has been transformed with a DNA sequence coding for the polypeptides having α-ALDCase activity, of which amino acid sequence is substantially from A to B of the amino acid sequence shown in FIG. 1.

The DNA strand according to the present invention can impart α-ALDCase producing ability to various microorganisms, for example, *Saccharomyces cerevisiae* to reduce its o-AL producing ability, or it can be effectively utilized in biotechnological production of α-ALDCase.

Also, since the yeast according to the present invention is such that its ability to produce α-AL (correctly leaking of α-AL out of the cell) is reduced, if the starting material liquor for fermentation is fermented with this yeast, the level of α-AL in the fermented liquor will become very low to give a result that the aging period required for treatment of α-AL in the fermented liquor, and therefore the production period of alcoholic beverage can be remarkably shortened. In the yeast of the present invention, its α-AL producing ability is reduced probably because the α-AL, even if produced within the cell in the fermentation process, will be converted to acetoin by α-ALDCase also produced within the cell.

Undesirable odors are problems also in production of fermentation products other than alcoholic beverages, such as vinegar. The undesirable odor in production of vinegars may also be ascribable to their content of DA, for example.

Accordingly, the DNA sequence coding for α-ALDCase in accordance with the present invention may also be used in such a way that acetic acid bacteria are transformed with the DNA sequence and the transformant thus produced is used in production of vinegars which are improved in their reduced undesirable odors.

BRIEF DESCRIPTION OF THE DRAWINGS

FIG. 1 illustrates the nucleotide sequence of the DNA strand according to the present invention and the amino acid sequence deduced from the nucleotide sequence;

DETAILED DESCRIPTION OF THE INVENTION

α-ALDCase gene

Definition

Figure 2:
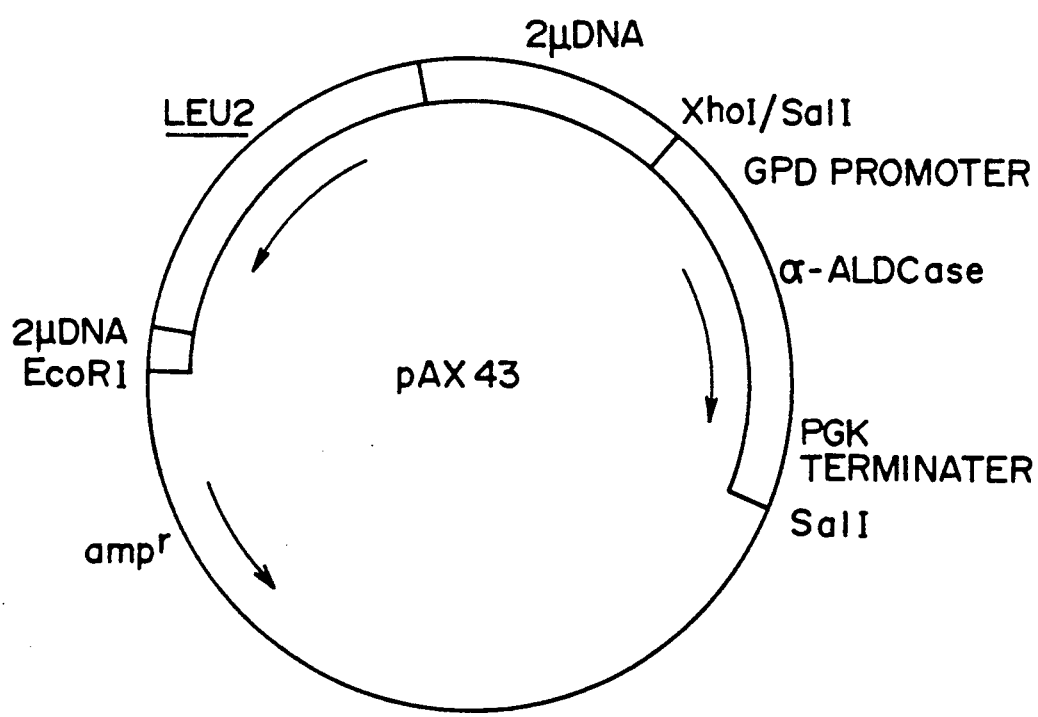
FIG. 2 illustrates the structure of pAX43.

The DNA sequence or strand, which will hereinbelow been sometimes called just as "DNA strand", according to the present invention having an ability in biotechnical production of α-ALDCase, namely the α-ALDCase gene, is one which has a nucleotide sequence which codes for a polypeptides having α-ALDCase activity, which amino acid sequence is substantially from A to B of the amino acid sequence shown in FIG. 1.

Here, the "DNA strand" means complementary double strands of polydeoxyribonucleic acid having a certain length. And, since the "DNA strand" is specified by the amino acid sequence of the polypeptides encoded thereby and the polypeptides has a finite length as mentioned above, the DNA strand also has a finite length. However, while the DNA strand contains a gene coding for α-ALDCase and is useful for biotechnological production of the polypeptides, such biotechnological production cannot be effected only by the DNA strand having the finite length, but biotechnological production of the polypeptides is rendered possible under the state where a DNA strand of a suitable length is linked upstream to its 5'-end and/or downstream to its 3'-end.

Accordingly, the "DNA strand" as mentioned in the present invention is inclusive, in addition to the DNA strand of a specific length (the length of A-B in terms of the corresponding amino acid sequence in FIG. 1), of those in the form of a linear DNA or a circular DNA strand containing the DNA strand of the specific length. This is why the DNA sequence in accordance with the present invention is defined as "having a nucleotide sequence coding for a polypeptides".

Of the existing forms of the DNA strand according to the present invention, typical are the plasmid form comprising the DNA strand as a part of the constituents and the form existing in a microorganism, particularly *E. coli*, yeast and acetic acid bacteria, as the plasmid form or the integrated form into the genome.

The preferable existing form of the DNA strand according to the present invention comprises the DNA strand of the present invention as a foreign gene linked to a promoter and a terminator so that the α-ALDCase gene can be expressed stably in a microorganism, which exists in the microorganism as a plasmid form or an integrated form into the genome. As the promoter and the terminator, known promoters and terminators can be used in a suitable combination.

Polypeptides encoded by the gene

As mentioned above, the DNA strand according to the present invention is specified by the amino acid sequence of the polypeptides encoded thereby. The polypeptides has α-ALDCase activity and has an amino acid sequence which is substantially from A to B of the amino acid sequence shown in FIG. 1. Here, "amino acid sequence which is substantially from A to B of the amino acid sequence shown in FIG. 1" indicates that some of the amino acids can be deleted or substituted or some amino acids can be added, etc., so long as the polypeptides has α-ALDCase activity.

A typical polypeptides having α-ALDCase activity in the present invention is of the amino acid sequence from A to B in FIG. 1, consisting of 235 amino acids, which amino acid sequence has not been known in the prior art.

As shown in the above, the statement "amino acid sequence which is substantially from A to B of the amino acid sequence shown in FIG. 1" indicates that some modification can be applied to the amino acid sequence. One example of a polypeptides which has such a modified amino acid sequence is one having an amino acid sequence of $A_1$ to B in FIG. 1, which amino acid sequence has 69 amino acids added upstream to the end A of the amino acid sequence from A to B in FIG. 1, namely has amino acids added corresponding to nucleotide sequence of from No. 212 to No. 418, since this polypeptides still has an α-ALDCase activity even though the activity is ca. 10% of that of the polypeptides having the amino acid sequence of from A to B in FIG. 1. Similarly, polypeptides having amino acid sequences of $A_2$ to B, $A_3$ to B, $A_4$ to B, $A_5$ to B and $A_6$ to B, respectively, wherein those having the amino acid sequences of $A_3$ to B, $A_5$ to B and $A_6$ to B, respectively, have N-terminus of Met instead of Val, fall within the scope of polypeptides in accordance with the present invention.

The present invention concerns basically with DNA strands, but the position of the present invention referred to hereinabove, namely the polypeptides which have amino acids added outside to the polypeptides of amino acid sequence A to B in FIG. 1 fall within the scope of polypeptides in accordance with the present invention tells, in turn, that the DNA strands which code for such "longer" polypeptides than that of amino acid sequence of A to B in FIG. 1 fall within the scope of the DNA strands in accordance with the present invention, since the nucleotide sequence encoding such longer polypeptides than that of amino acid sequence of A to B in FIG. 1 does have the nucleotide sequence encoding the polypeptide of amino acid sequence of A to B.

Nucleotide sequence of DNA strand

The DNA strand coding for α-ALDCase is one having the nucleotide sequence from A to B in FIG. 1 or one of those having nucleotide sequences corresponding to the changes in amino acid sequence of α-ALDCase as mentioned above or degenerative isomers thereof. Here, the "degenerative isomer" means a DNA strand which is different only in degenerative codon and can still code for the same polypeptides. For example, relative to the DNA strand having the nucleotide sequence of A to B in FIG. 1, the DNA strand having a codon corresponding to any one of the amino acids changed from, for example, the codon (GGC) corresponding to Gly at the carboxy terminal end to, for example, GGT which is in degenerative relationship therewith, is called a degenerative isomer in the present invention.

A preferable specific example of the DNA strand according to the present invention has at least one stop codon (e.g. TGA) in contact with the 3'-end.

Further, upstream to the 5'-end and/or downstream to the 3'-end of the DNA strand of the present invention, a DNA strand with a certain length can be continuous as the non-translation region (the initial portion downstream to the 3'-end is ordinarily a stop codon such as TGA).

The nucleotide sequence of the DNA strand shown in FIG. 1 was determined for the gene coding for the α-ALDCase cloned from Acetobacter aceti subspecies xylinum IFO 3288 according to the dideoxy method.

Acquirement of DNA strand

One means for obtaining the DNA strand having the nucleotide sequence coding for the amino acid sequence of the above α-ALDCase is to synthesize chemically at least a part of the DNA strand according to the method for synthesis of polynucleotide.

It would, however, be preferable to obtain the DNA strand from the genomic library of *Acetobacter aceti subspecies xylinum* IFO 3288 according to the method conventionally used in the field of genetic engineering, for example, the hybridization method with the use of a suitable probe.

In this invention, the present inventors cloned the DNA strand of the present invention from the above genomic library by use of the shot gun method, because the nucleotide sequence coding for the α-ALDCase of *Acetobacter aceti subspecies xylinum* IFO 3288 and the amino acid sequence of α-ALDCase were not known (see Examples shown below about its details).

Yeast having ability to produce α-ALDCase

The DNA strand of the present invention cloned as described above contains the genetic information for making α-ALDCase, and therefore this can be introduced into the yeast used generally as the yeast for fermentation of alcoholic beverages (*Saccharomyces cerevisiae*) to transform the yeast, whereby a yeast for fermentation having α-ALDCase producing ability, namely with reduced α-AL producing ability, can be obtained.

Yeast

The yeast to be transformed in the present invention may be a yeast belonging to *Saccharomyces cerevisiae* as described in "The Yeasts, a Taxonomic Study" third edition (Yarrow, D., ed. by N. J. W. Kreger-Van Rij. Elsevier Science Publishers B. V., Amsterdam (1984), p.379) and its synonym or a mutant, but for the purpose of the present invention, a yeast for fermentation of alcoholic beverages belonging to *Saccharomyces cerevisiae*, specifically beer yeast, wine yeast, sake yeast, etc., are preferred. Specific examples may include wine yeast: ATCC 38637, ATCC 38638, IFO 2260 (wine yeast OC2); beer yeast: ATCC 26292, ATCC 2704, ATCC 32634; saké yeast: ATCC 4134, ATCC 26421, IFO 2347 (Saké yeast Kyokai #7), etc.

To further comment on the properties of these yeasts for fermentation, as the result of selection and pure cultivation over long years for the properties suitable for fermentation, namely efficient fermentation of the starting material liquid for fermentation, production of alcoholic beverages with good flavor and stable genetic properties, etc., as the index, they have become polyploids which will undergo genetically cross-segregation with extreme difficulty and have lost spore forming ability substantially completely. For example, in the case of beer yeast practically used, while it is enhanced in the ability to assimilate maltose, maltotriose which are sugar components in the wort, it has lost its wild nature, for example, it is crystal violet sensitive, etc.

Transformation

It has been confirmed for the first time by the present inventors that transformation of a yeast with the DNA strand of the present invention resulted in reduction of its α-AL producing ability. However, the procedure or the method itself for preparation of the transformant can be one conventionally employed in the field of molecular biology, bioengineering or genetic engineering, and therefore the present invention may be practiced according to these conventional techniques except for those as described below.

For expression of the gene of the DNA strand of the present invention in a yeast, it is first required that the gene be carried on the plasmid vector which is stable in the yeast. As the plasmid vector to be used in this operation, all of the various kinds known in the art such as YRp, YEp, YCp, YIp, etc., can be used. These plasmid vectors are not only known in literatures, but also they can be constructed with ease.

On the other hand, for the gene of the DNA strand of the present invention to be expressed in a yeast, the genetic information possessed by the gene is required to be transcribed and translated. For that purpose, as the unit for controlling transcription and translation, a promoter and a terminator may be linked upstream to the 5'-end and downstream to the 3'-end of the DNA strand of the present invention, respectively. As such promoter and terminator, various kinds such as ADH, GAPDH or GPD, PHO, GAL, PGK, ENO, TRP, HIP, etc., have been already known in the art and any of these can be utilized also in the present invention. These are not only known in literatures, but also they can be prepared with ease.

As the marker for selecting the transformant to be obtained by the present invention, a resistant gene to G418, hygromycin B, a combination of methotrexate and sulfanylamide, tunicamycin, ethionine, compactin, copper ion, etc., can be employed.

For having the DNA strand of the present invention held more stably in a yeast, the DNA strand can be integrated into the genome of the yeast. In this case, for making easier integration of the DNA strand of the present invention carried on the plasmid vector into the genome, it is desirable to insert a DNA having high homology with the genome DNA into the plasmid vector, and examples of DNA for this purpose may include rRNA gene, HO gene, etc.

Among them, it has been known that rRNA gene is repeated tandemly for about 140 times in haploid yeast genome (Journal of Molecular Biology 40, 261–277 (1969)). Due to this specific feature, when this sequence is utilized as the target sequence for recombination, there are the following advantages obtainable as compared with the case when utilizing other gene sequence.
1. It is expected that the transformation frequency may be elevated.
2. The change in the corresponding trait of the target sequence by recombination may be considered to be negligible.
3. It becomes possible to integrate a plural number of foreign genes into the genome by repeating a series of operations of integration of plasmid and excision of the vector sequence.

Also, the DNA strand which can be used for transformation of a yeast in the present invention can also code for a polypeptides different from the polypeptides of A to B shown in FIG. 1, so long as it has α-ALDCase activity, as mentioned previously.

Transformation of a yeast with the plasmid thus prepared can be done according to any method suited for the purpose conventionally used in the field of genetic engineering or bioengineering, for example, the spheroplast method [Proceedings of National Academy of Sciences of the U.S.A. (Proc. Natl. Sci. USA), 75, 1929 (1978)], the lithium acetate method [Journal of Bacteriology (J. Bacteriol.), 153, 163 (1983)], etc.

The yeast of the present invention thus obtained is the same as the yeast before transformation in its geno type or phenotype except for the new trait according to the genetic information introduced by the DNA strand of the present invention (that is, endowed with α-ALDCase producing ability to consequently decompose α-AL within the cell, thereby lowering the amount of α-AL leaked out of the cell), the trait derived from the vector used and the defective corresponding trait due to the defect of a part of the genetic information during recombination of the gene which might have occurred. Further, the beer yeast obtained by integrating the DNA strand of the present invention into the yeast genome by use of YIp type plasmid, followed by excision of unnecessary vector sequence has no trait inherent in the vector employed. Accordingly, the yeast according to the present invention can be used under essentially the same fermentation conditions for the yeast for fermentation of the prior art. It is possible, on the other hand, to reduce α-AL production in the fermented liquor, and therefore the α-AL content in the fermented liquor is consequently low, whereby the aging period of the fermented liquor required for its treatment can be remarkably shortened.

Production of alcoholic beverages

The use of the yeast in accordance with the present invention in fermentation of materials for fermentation will result in production of alcoholic beverages with the advantages referred to above.

The types of materials for fermentation depend, of course, on the type of alcoholic beverages to be produced, and wort is used for beer production, and fruit juice, particularly grape juice, for wine.

Yeast can be in a slurry, in an immobilized state or in any suitable state or form. Fermentation conditions can also be those conventionally used with conventional yeasts.

The alcoholic beverages produced have a lower content of α-AL thanks to the use of the yeast of the present invention which is endowed with capability of α-ALDCase production, and the time required for producing alcoholic beverages having lower DA odor by aging is significantly reduced, as referred to hereinabove.

EXPERIMENTAL EXAMPLES (1) Cloning of α-ALDCase gene (i) Purification of chromosomal DNA of α-ALDCase producing strain By culturing over night under aeration *Acetobacter aceti subspecies xylinum* IFO 3288 (procured from Institute for Fermentation, Osaka, Japan) in 100 ml of YPD medium containing 1% yeast extract, 2% peptone and 2% glucose, 0.7 g of wet microorganism cells was obtained.

This was resuspended in 30 ml of a buffer [50 mM Tris-HCl (pH 8.0) and 50 mM EDTA]. Subsequently, it was treated with 400 µg/ml of lysozyme (produced by Seikagaku Kogyo), and 10 µg/ml of ribonuclease A (produced by Sigma Co.) at 37° C. for 15 minutes, to which were then added 70 ml of a buffer (50 mM Tris-HCl (pH 8.0) and 50 mM EDTA). Next, it was treated with 0.5% of sodium dodecylsulfate (SDS) and 50 µg/ml of proteinase K (produced by Sigma Co.) at 65° C. for 30 minutes.

The product was then subjected to extraction twice with phenol and once with phenol-chloroform (1:1). DNA was precipitated with ethanol, and then dissolved in 5 ml of TE buffer (10 mM Tris-HCl (pH 8.0), 1 mM EDTA). The solution was treated with 100 µg of ribonuclease A at 37° C. for 1 hour, and then subjected to extraction once with phenol and with phenol-chloroform (1:1). DNA was precipitated with ethanol, then dissolved in 2 ml of TE buffer. The solution was then dialyzed against 1 liter of TE buffer. 360 µg of chromosomal DNA was obtained (ii) Preparation of a cosmid library The chromosomal DNA (11 µg) obtained in (i) was partially digested to ca. 40 kb with a restriction enzyme Sau3AI. The DNA fragments obtained were ligated with 4.2 µg of BamHI-cleaved cosmid pJB 8 arm (Amersham) by a T4 ligase. The DNA was in vitro packaged into λ particles by means of in vitro packaging kit (Amersham), and was used to transfect *E. coli* DHI (F−, gyr A96, rec Al, rel Al?, end Al, thi-1, hsd R17, sup E44, λ−) [*J. Mol. Biol.*, 166, 557–580 (1983)] to obtain a cosmid library.

(iii) Screening of an α-ALDCase gene carrying strain

An α-ALDCase gene carrying strain was obtained by selecting strain which exhibits α-ALDCase activity from the cosmid library obtained in (ii).

Specifically, 600 strains from the cosmid library were respectively inoculated into an L-broth containing 50 µg/ml of ampicillin and 0.5% of glucose and aerobically cultivated overnight at 37° C., and α-ALDCase activity was measured for each culture. In other words, collected cells were suspended in a 30 mM potassium phosphate buffer (pH 6.2). Toluene (10 µl) was added to the cell suspension, and the suspension was vigorously mixed by vortexing for 30 seconds. The α-ALDCase activity of the cell suspension was evaluated according to the method of Godfredsen et al. [*Carlsberg Res. Commun.*, 47, 93 (1982)]. As a result, two α-ALDCase activity carrying strains were obtained. The plasmids of the clones obtained were respectively designated as pAX1 and pAX2.

(iv) Determination of the DNA base sequence in α-ALDCase gene

Figure 3:
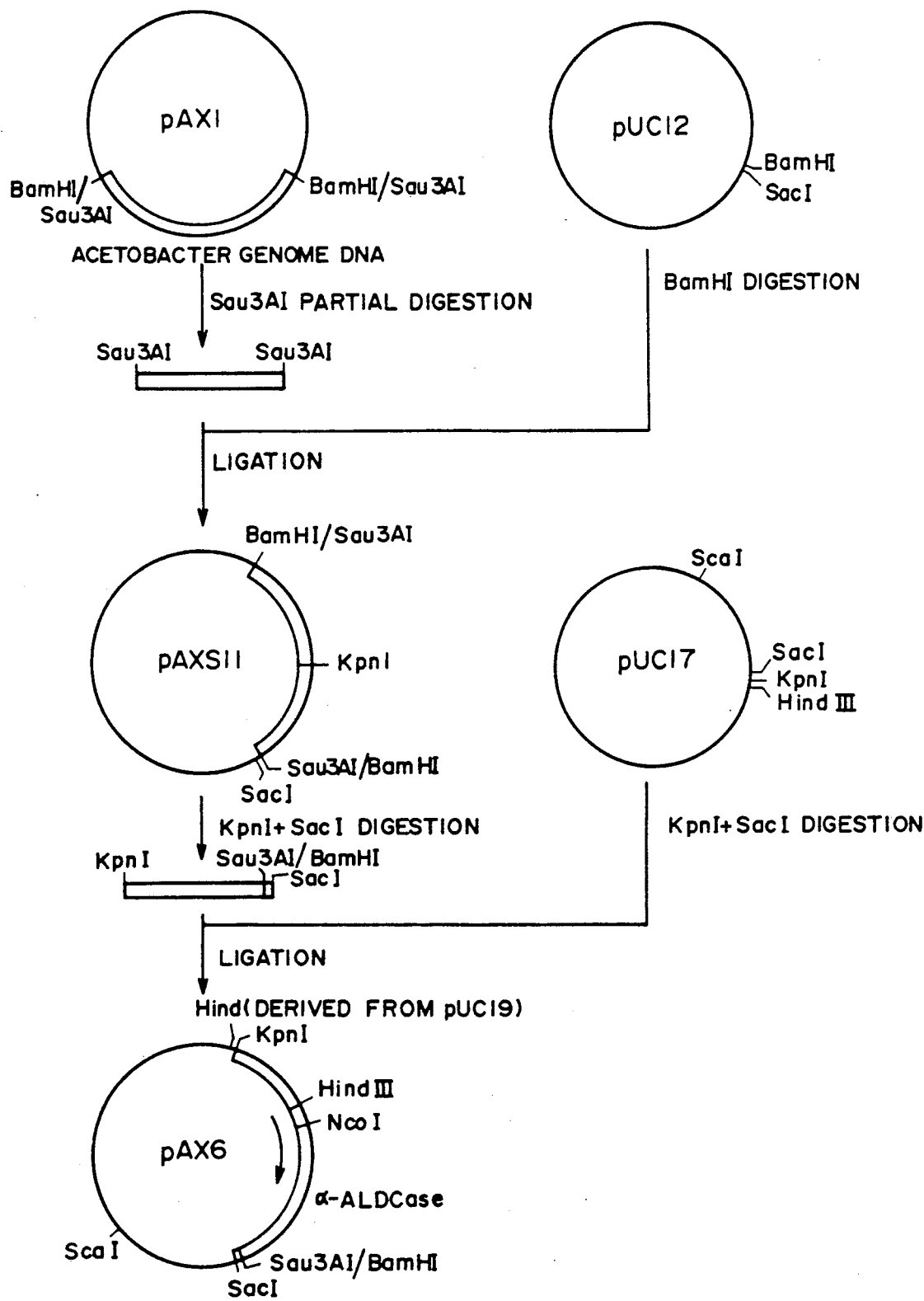
FIG. 3 is a flow chart for sub-cloning the α-ALDCase gene.

Subcloning of the α-ALDCase gene was carried out by the method schematically illustrated in FIG. 3. First, the DNA fragment which was obtained by the partial digestion of pAX1 with Sau3AI was inserted into the BamHI site of pUC12 (Pharmacia). One of the plasmids thus obtained exhibited α-ALDCase activity in *E. coli* and contained a chromosomal DNA fragment of 3.6 kb. The plasmid was designated pAXS11. A fragment of ca. 1260 bp excised from the pAXS11 with KpnI and SacI was inserted between the KpnI site and the SacI site of pUC19 (Takara Shuzo) to obtain a plasmid (pAX6). The *E. coli* carrying the pAX6 exhibited α-ALDCase activity.

The DNA base sequence (from the base at the position 1 to the base at the position 1252 in FIG. 1) of the KpnI-Sau3AI fragment contained in the pAX6 was determined by the dideoxy method [*Proc. Natl. Acad. Sci. USA*, 74, 5463 (1977)]. As the result of the analysis of the base sequence, it was found that the fragment contained an open reading frame of 912 bp which was capable of coding for a protein having a molecular weight of 33,747.

(2) Introduction of the α-ALDCase gene into yeast (Part 1)

(i) Acquirement of the GPD promoter

A chromosomal DNA was prepared in a usual manner from *Saccharomyces cerevisiae* S288C [(α, suc2, mal, gal2, CUP1): *Biochem. Biophys. Res. Commun.*, 50 1868 (1973): ATCC26108]. The DNA was partially digested with Sau3AI under such a condition as to primarily produce fragments of ca. 10 kb and then cloned into BamHI site of the plasmid pBR322 (Takara Shuzo) to obtain a library.

Figure 4:
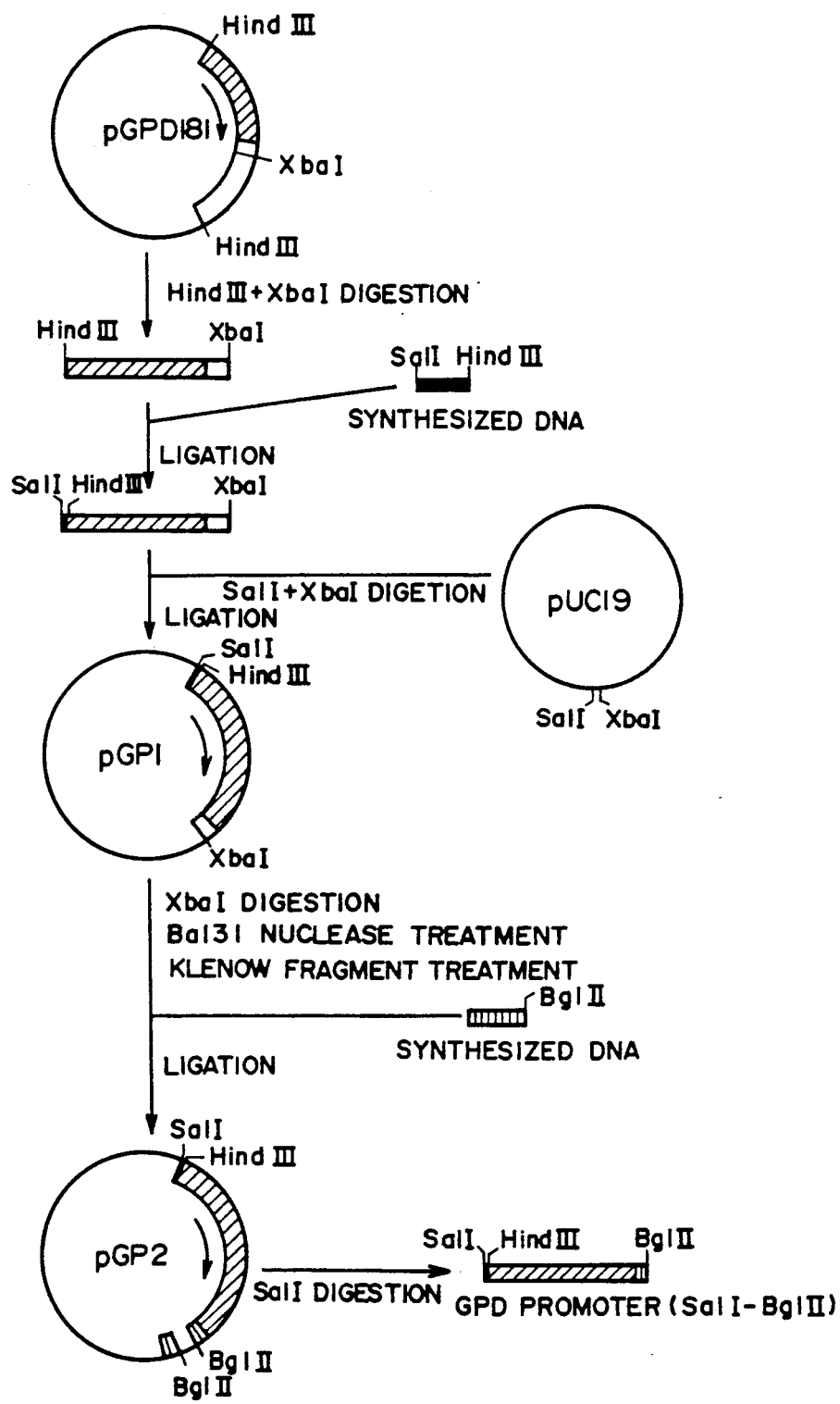
FIG. 4 is a flow chart for obtaining GPD promoter (SalI-BglII)

A synthesized oligomer corresponding to the bases region of the GPD gene [*J. Biol. Chem.*, 254, 9839 (1979)] was end-labelled with 32P, and the labelled oligomer was used as a probe to obtain a clone containing the GPD gene from the library. The plasmid DNA obtained from the clone was digested with HindIII and a HindIII fragment of ca. 2.1 kb was inserted into a HindIII site of pUC18 (Pharmacia) to obtain plasmid pGPD181. Then, GPD promoter (SalI-BglII) was acquired according to the method illustrated schematically in FIG. 4. First of all, the pGPD181 was cleaved with restriction enzymes HindIII and XbaI to obtain a HindIII-XbaI fragment containing the promoter region of the GPD gene (illustrated by a hatched box in FIG. 4) and a part of the coding region To the HindIII cohesive end of this fragment was ligated synthetic double-stranded DNA having the following nucleotide sequence. This synthetic double-stranded DNA contains the PstI and SphI sites and the cohesive ends of SalI and HindIII.

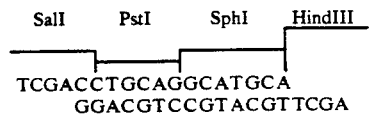

The HindIII cohesive end was successfully changed into the SalI cohesive end by the addition of the synthetic double-stranded DNA.

Next, this fragment was inserted between the SalI cleavage site and the XbaI cleavage site of the pUC19.

The plasmid pGP1 thus obtained was digested with XbaI, followed by the Ba131 nuclease digestion to remove completely the coding region and end-filling with Klenow fragment (Takara Shuzo). To this blunt end produced was ligated a synthetic double-stranded DNA of the following nucleotide sequence. (The synthetic double-stranded DNA has a cohesive end of BglII on its one end.)

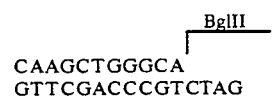

Figure 5:
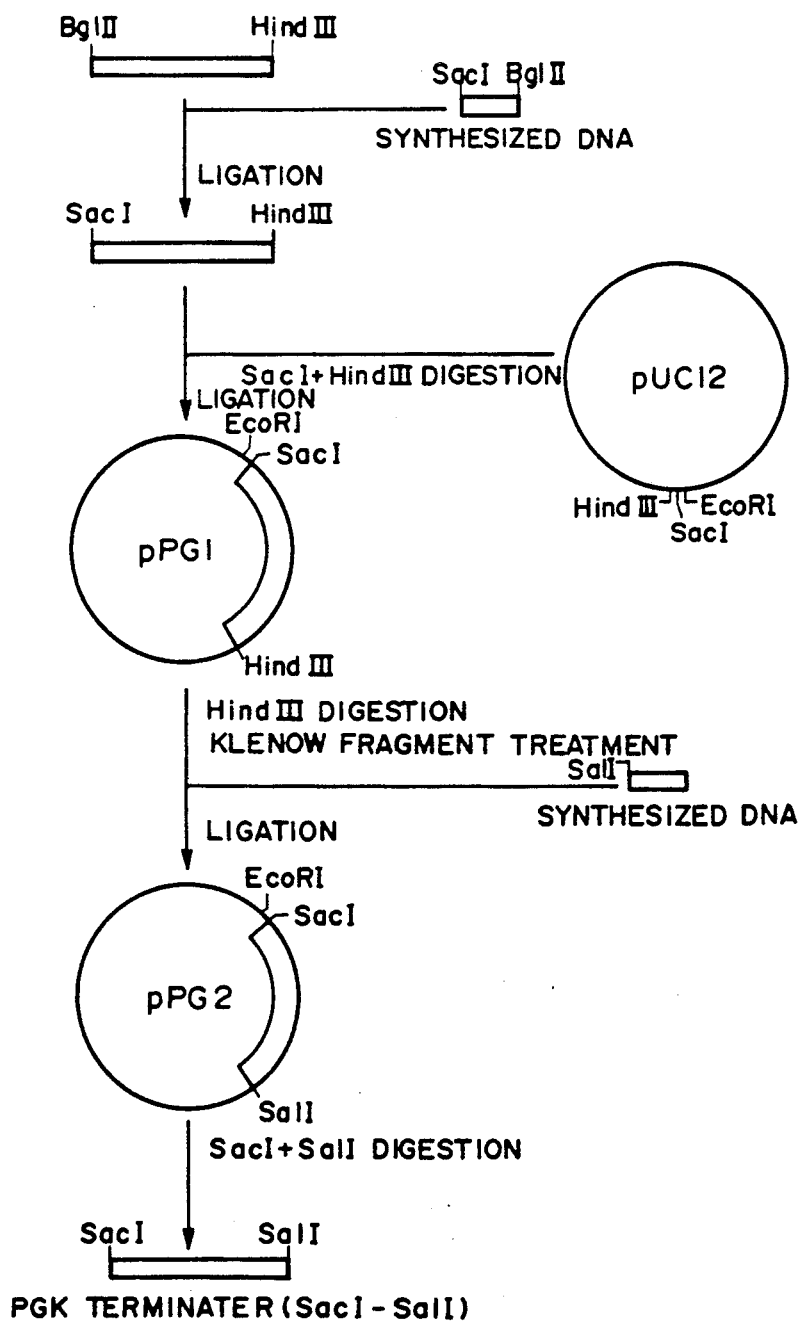
FIG. 5 is a flow chart for obtaining PGK terminator (SacI-SalI)

The blunt end was successfully changed into the BglII terminus by the addition of the synthetic double-stranded DNA. Then the SalI-BglII fragment containing the GPD promoter which was obtained by digesting with SalI was designated as GPD promoter (SalI-BglII) (ii) Acquirement of the PGK terminator PGK gene [*Nucl. Acids Res.*, 10, 7791 (1982)] was cloned from the library prepared in Example (2)-(i) by the same manner as in Example (2)-(i). As a probe, a synthetic oligonucleotide which corresponded to the nucleotides from position 1 to position 28 in the coding region of the PGK gene and was labelled at the terminus with 32P was used. The plasmid DNA obtained from this clone was digested with HindIII to obtain a 2.9 kb fragment containing the PGK gene. The fragment was further digested with BglII to obtain a 375 bp BglII-HindIII fragment containing the terminator region of the PGK gene and a part of the coding region. The PGK terminator was prepared from this fragment according to the method illustrated schematically in FIG. 5. First of all, to the BglII cohesive end of the fragment was ligated a synthetic double-stranded DNA of the following sequence. This synthetic double-stranded DNA contains SmaI site and the cohesive ends of SacI and BglII.

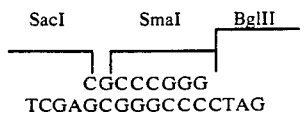

Next, the thus obtained SacI-HindIII fragment containing PGK terminator region was inserted between the HindIII site and the SacI site of pUC12 to construct plasmid pPG1. The pPG1 was then digested with HindIII and treated with Klenow fragment to make a blunt end. To this blunt end was ligated a synthetic double-stranded DNA of the following nucleotide sequence, which synthetic double-stranded DNA contains the cohesive end of SalI.

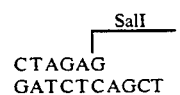

Plasmid pPG2 was constructed by the re-ligation after addition of the synthetic DNA. A SacI-SalI fragment containing a terminator part can be prepared from pPG2 by the SacI and SalI digestions. This fragment was designated PGK terminator (SacI-SalI).

(iii) Construction of an expression plasmid and its introduction into yeast

Figure 6:
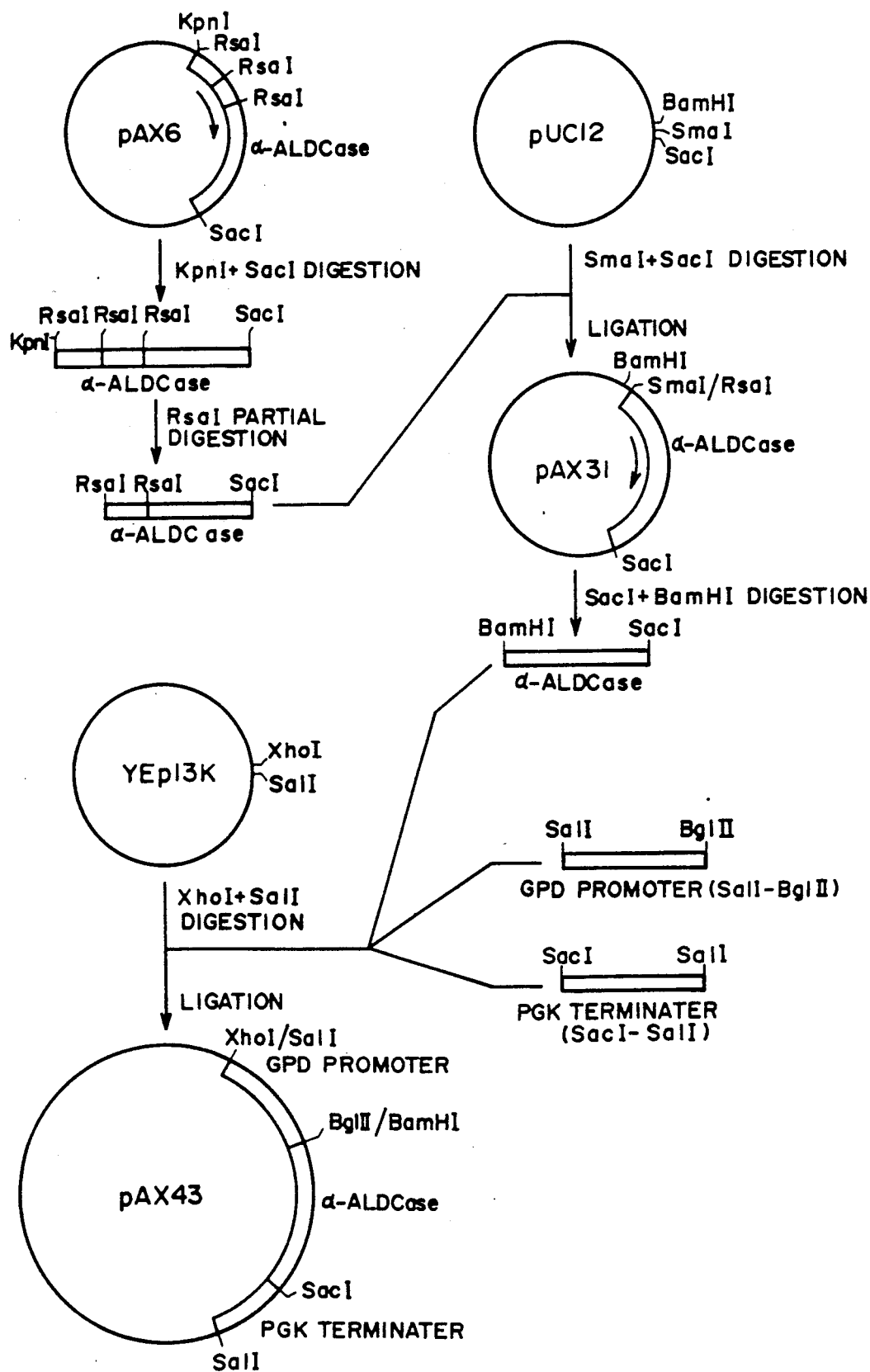
FIG. 6 is a flow chart for constructing pAX43.

Plasmid pAX43 which expresses an α-ALDCase gene in yeast was constructed according to the method illustrated schematically in FIG. 6. First, the plasmid pAX6 constructed in Example (1)-(iv) was digested with KpnI and SacI to obtain an about 1260 bp KpnI-SacI fragment containing the α-ALDCase gene. This fragment was partially digested with RsaI to obtain a 1.02 kb RsaI-SacI fragment containing the α-ALDCase gene illustrated in FIG. 1. This fragment was inserted between the SmaI and SacI sites to construct plasmid pAX31. This plasmid was digested with BamHI and SacI to obtain a BamHI-SacI fragment containing the α-ALDCase gene, which fragment contains the nucleotide sequence from position 243 to position 1252 of the nucleotide sequence illustrated in FIG. 1 and a partial nucleotide sequence of the vector. Three fragments, i.e. this fragment, the GPD promoter (SalI-BglII) obtained in (2)-(i) and the PGK terminator (SacI-SalI) obtained in (2)-(ii), were inserted between the XhoI and SalI sites of the plasmid YEp13K (described in detail hereinafter) to construct the expression plasmid pAX43 (FIG. 2). This plasmid pAX43 was introduced into a yeast [a TD4 (a, his, ura, leu, trp) strain which is a mutant of *Saccharomyces cerevisiae* S288C]by the lithium acetate method [*J. Bacteriol.*, 153, 153, 1983)]. The TD4 strain containing pAX43 obtained in such a way is referred to as YAL12.

The plasmid YEp13K was prepared in such a procedure as follows by using basically plasmid YEp13 replicable in yeast [*Gene*, 8, 121 (1979)].

First of all, the SalI-SacI fragment and the XhoI-SmaI fragment which were placed at either end of the LEU2 of the plasmid YEp13 were removed. By this procedure, the plasmid obtained had no cleavage sites for restriction enzymes XhoI, SacI, SmaI and BglII, but had only one cleavage site for restriction enzyme SalI. Next, the synthetic oligonucleotide 41mer was inserted into the plasmid between the cleavage site of restriction enzyme HindIII derived from pBR322 and the cleavage site of restriction enzyme HindIII derived from 2μm DNA. This synthetic oligonucleotide had cleavage sites of restriction enzymes SacI, SmaI, BglII and XhoI and also possessed the following base sequence, the resultant plasmid being designated YEp13K.

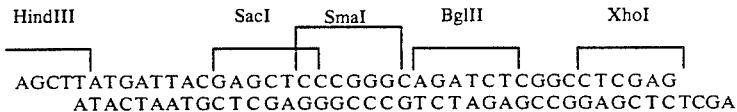

(iv) Expression of the α-ALDCase gene in yeast

The TD4 containing YEp13K and a YAL2 (TD4 strain containing pAX43) were respectively cultured overnight in the selection medium [0.7% amino acid free yeast nitrogen base (manufactured by DIFCO Co.), 2% glucose, 20 mg/lit histidine, 20 mg/lit tryptophan, 20 mg/lit uracil], and then their α-ALDCase activities were measured. The results are shown in the following table.

The α-ALDCase activity of yeast was measured by the method described by Godfredsen et al. wherein bacterial cells ground by means of glass beads were used as an enzyme solution. 1U of the activity means the amount of an enzyme which will produce 1 μmole acetoin per hour. The amount of protein of the enzyme solution was determined with a Protein Assay Kit (manufactured by Bio-Rad Co.).

The α-ALDCase is expressed as the unit per protein amount in the enzyme solution (U/mg protein)

| α-ALDCase activity of YAL2 | | |
|---|---|---|
| Strain | | α-ALDCase activity (U/mg protein) |
| TD4 + YEp 13K | 1 | 0 |
| | 2 | 0 |
| | Average | 0 |
| YAL2 | 1 | 2.50 |
| (TD4 + pAX43) | 2 | 3.27 |
| | 3 | 3.68 |
| | 4 | 3.47 |
| | Average | 3.23 |

(3) Introduction of the α-ALDCase gene into yeast (Part 2)

(i) Acquirement of the ADH1 promote

A clone containing the ADH1 gene was obtained from the library prepared in Example (2)-(i) by using as a probe a 32P terminus labelled synthetic oligonucleotide which corresponded to the bases from position 7 to position 36 in the coding region of the ADH1 gene [*J. B. C.*, 257, 3018 (1982)]. The DNA fragment obtained from this clone was partially digested with a restriction enzyme Sau3AI to obtain the 1.5 kb DNA fragment containing a part of the coding region and the promoter of ADH1 gene.

This fragment was inserted into the BamHI site of plasmid pUC18 (Pharmacia), and the plasmid obtained was designated pADHSl. The BamHI site of the pUC18 is placed between the XbaI and SmaI of pUC18, and thus the DNA fragment inserted into the BamHI site can be excised by digestion with XbaI and SmaI. After the plasmid pADHSl had been digested with XbaI, it was treated with an endonuclease Ba131 to remove completely the coding region of the ADH1 gene and HindIII linkers (Takara Shuzo) were ligated to the fragment. Then, after digesting with SmaI, BamHI linkers were ligated to the fragment The resultant BamHI-HindIII fragment was used as ADH1 promoter The ADH1 promoter was inserted between the BmaHI and HindIII sites in YEp13K to obtain the plasmid pYADH.

(ii) Expression of the α-ALDCase gene

After pAX6 had been digested with restriction enzyme XbaI, it was treated with a Klenow fragment to make a blunt end, and plasmid pAX6Bg was prepared by linking BglII linkers (Takara Shuzo) and re-ligation. From this pAX6Bg, the HaeIII-BglII fragment (containing a base sequence from position 180 to position 1252 of the base sequence illustrated in FIG. 1 and a part of the vector) which contained the ALDCase gene was obtained (referred to hereinafter as fragment 1).

After the SacI terminus of the RsaI-SacI fragment obtained in Example (2)-(iii) was treated with a Klenow fragment to form a blunt end, BglII linkers were ligated to it. This RsaI-BglII fragment (containing a base sequence from position 243 to position 1252 of the base sequence illustrated in FIG. 1 and a part of the vector) was designated fragment 2. From the pAX6Bg, the HindIII-BglII fragment (containing a base sequence from position 345 to position 1252 of the base sequence illustrated in FIG. 1 and a part of the vector) which contained a part of the α-ALDCase gene was also obtained (referred to hereinafter as fragment 3).

The plasmid pYADH was digested with HindIII and treated with Klenow fragment to form a blunt end, and it was further digested with BglII. This fragment was linked to the aforementioned fragment 1 or 2 to prepare plasmids pAX39 (in the case of fragment 1) and pAX40 (in the case of fragment 2), respectively. The fragment 3 was inserted between the HindIII and BglII sites of pYADH to prepare a plasmid pAX41.

The plasmids pAX39, pAX40 and pAX41 can produce polypeptides which are encoded by the fragments 1, 2 and 3, respectively, with the use of the ADHl promoter These pAX39, pAX40 and pAX41 were respectively used to transform TD4, and the α-ALDCase activities of the transformants obtained were measured The results are shown in the following table.

| Comparison of α-ALDCase activities | |
|---|---|
| Strain | Ratio of α-ALDCase activities |
| TD4 + YEp13K | 0 |
| TD4 + pAX39 | 69 |
| TD4 + pAX40 | 100 |
| TD4 + pAX41 | 0 |

The polypeptide encoded in the fragment 2 is the polypeptide which is illustrated as the part from $A_2$ to B in FIG. 1. The polypeptide encoded in the fragment 1 is a polypeptide which is illustrated as the part from $A_1$ to B in FIG. 1.

The polypeptide obtained by the expression of the fragment 3 showed no α-ALDCase activity It was supposedly attributed to the reason that only a short peptide comprising amino acids corresponding to the base sequence from position 352 to position 372 in FIG. 1 is presumably produced (the ATG from position 352 to position 354 is suspected to be a translation initiating codon and the TGA from position 373 to position 375 to be a terminating codon), and this peptide was quite different from the α-ALDCase, so that it showed no α-ALDCase activity.

(4) Introduction of the α-ALDCase qene into yeast (Part 3)

Expression of the DNA sequence which codes for α-ALDCase which has an amino acid sequence of a part from A to B in FIG. 1 and to which several amino acids have been added.

(i) Introduction

Referring in detail to the base sequence illustrated in FIG. 1, some ATG's or GTG's are present upstream to and in the same reading frame as the nucleotide sequence coding for the α-ALDCase. These ATG and GTG codons are possible translation initiation points. They are underlined and are numbered 1 to 7. Any one of these codons may be selected for use as translation initiation point. Translation will start at the selected point so that a protein is produced in yeast having an amino acid sequence represented by the sequence from A to B in FIG. 1 to the N-terminus of which several amino acids have been added. The exact number of the extra amino acids is dependent on which ATG is chosen as the translation start point. When GTG codon is selected, it is necessary to convert it to ATG, as GTG is not recognized as an initiation codon in yeast. The number of amino acids to be added depends upon which ATG or GTG is selected as the translation initiation point. α-ALDCase polypeptide with extra amino acids were produced by the methods specified in section (ii) to (v) below, and it was proved that these polypeptides have α-ALDCase activities.

(ii) Introduction of a new restriction site into pAX6 by a site specific mutagenesis method (resulting in the construction of 5 plasmids designated pALDC1-5)

Oligonucleotides A-E shown in Table 1 were synthesized.

TABLE 1

| Oligonucleotide | Nucleotide sequence | Mutagenized plasmid | Expression plasmid |
|---|---|---|---|
| A | 5'-TCCATATATTTTTATATATGGAAATAGG-3'<br>. . . 1<br>5'-TCCATATATTTTTAAAATGGAAATAGG-3'<br>└────┘<br>DraI | pALDC1 | pAX50A |
| B | 5'-TTAGTCTGCAATCACAAATGACCGGGT-3'<br>. . . 2<br>5'-TTAGTCTGCAATTTAAAATGACCGGGT-3'<br>└────┘<br>DraI | pALDC2 | pAX50B |
| C | 5'-GGTTGAGGCGATGCCATGTGCCGCATTGTC-3'<br>. . . . . 3<br>3'-CCAACTCCGCTAAATTTTACGGCGTAACAG-5'<br>└────┘<br>DraI | pALDC3 | pAX50C |
| D | 5'-GTGCCGCATTGTCCCCCGATGCAGGAGACT-3'<br>. . . . . 4<br>3'-CACGGCGTAACAAAATTTACGTCCTCTGA-5'<br>└────┘<br>DraI | pALDC4 | pAX50D |

TABLE 1-continued

| Oligonucleotide | Nucleotide sequence | Mutagenized plasmid | Expression plasmid |
|---|---|---|---|
| E | 5'-ATGCAGGAGACTGAGGTC<u>GTG</u>AAGCTTAAAT-3'<br>. . . . . . . . 5<br>3'-TACGTCCTCTGAAAATTT<u>TAC</u>TTCGAATTTA-5'<br>⌊___⌋<br>DraI | pALDC5 | pAX50E |

Figure 7:
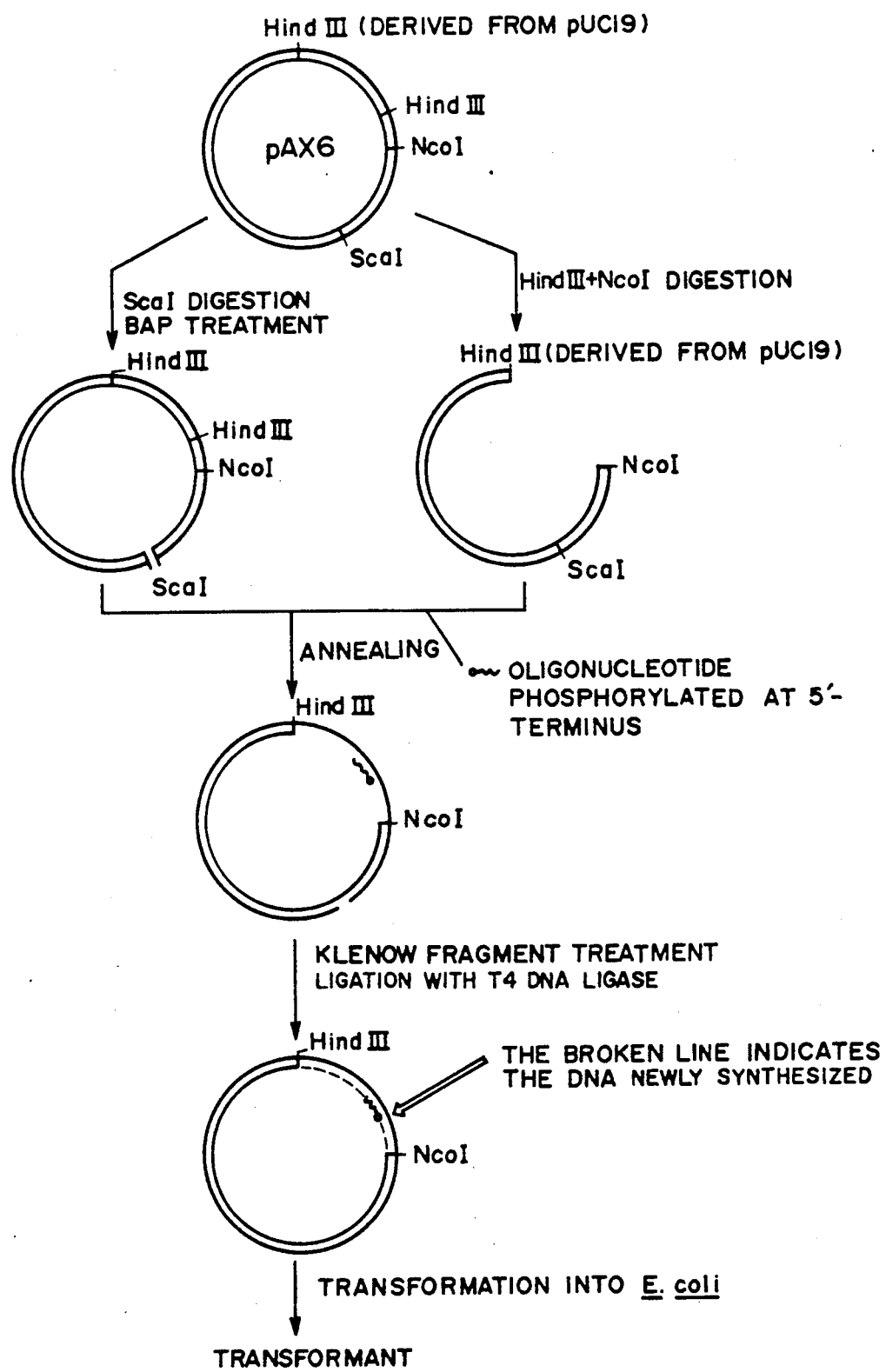
FIG. 7 illustrates site-specific mutation.

Five (5) pairs of the nucleotide sequence are shown in Table 1. The nucleotide sequences of the synthesized oligonucleotides to be used for site-specific mutagenesis are shown in the lower row of each pair. The nucleotide sequences of pAX6 to be mutagenized with these oligonucleotides are shown in the upper rows. The nucleotide sequences to be mutagenized include some of possible translation start points which are underlined and numbered 1 to 5 in FIG. 1. The nucleotide sequences in the lower rows are the same as the modified nucleotide sequences obtained after the mutation, wherein the nucleotides modified are shown with a dot (·) added. The mutation creates DraI cleavage site immediately upstream to the codons which are underlined and numbered 1 to 5 in FIG. 1. Further, when the underlined codon is GTG, it was converted into ATG. The plasmid pAX6 was mutagenized by means of these oligonucleotides shown in Table 1 by site-specific mutagenesis (Morinaga, Y. et al., Bio/Technology, 2, 636–639 (1984)) as outlined in FIG. 7. The names of mutated plasmids and expression plasmids constructed therefrom are set forth in Table 1. Construction of the expression plasmids are described in detail in Example (iv). A fragment containing α-ALDCase gene was excised from the mutated plasmid with DraI+SacI.

(iii) Creation of new restriction sites in pAX6 by means of a synthesized double stranded DNA (Construction of pALDC6 and 7)

Two double stranded DNAs, F and G, shown in Table 2 were synthesized.

containing the α-ALDCase gene were excised with DraI+SacI from pALDC6 and pALDC7, respectively.

(iv) Acquirement of GPD promoter

Figure 8:
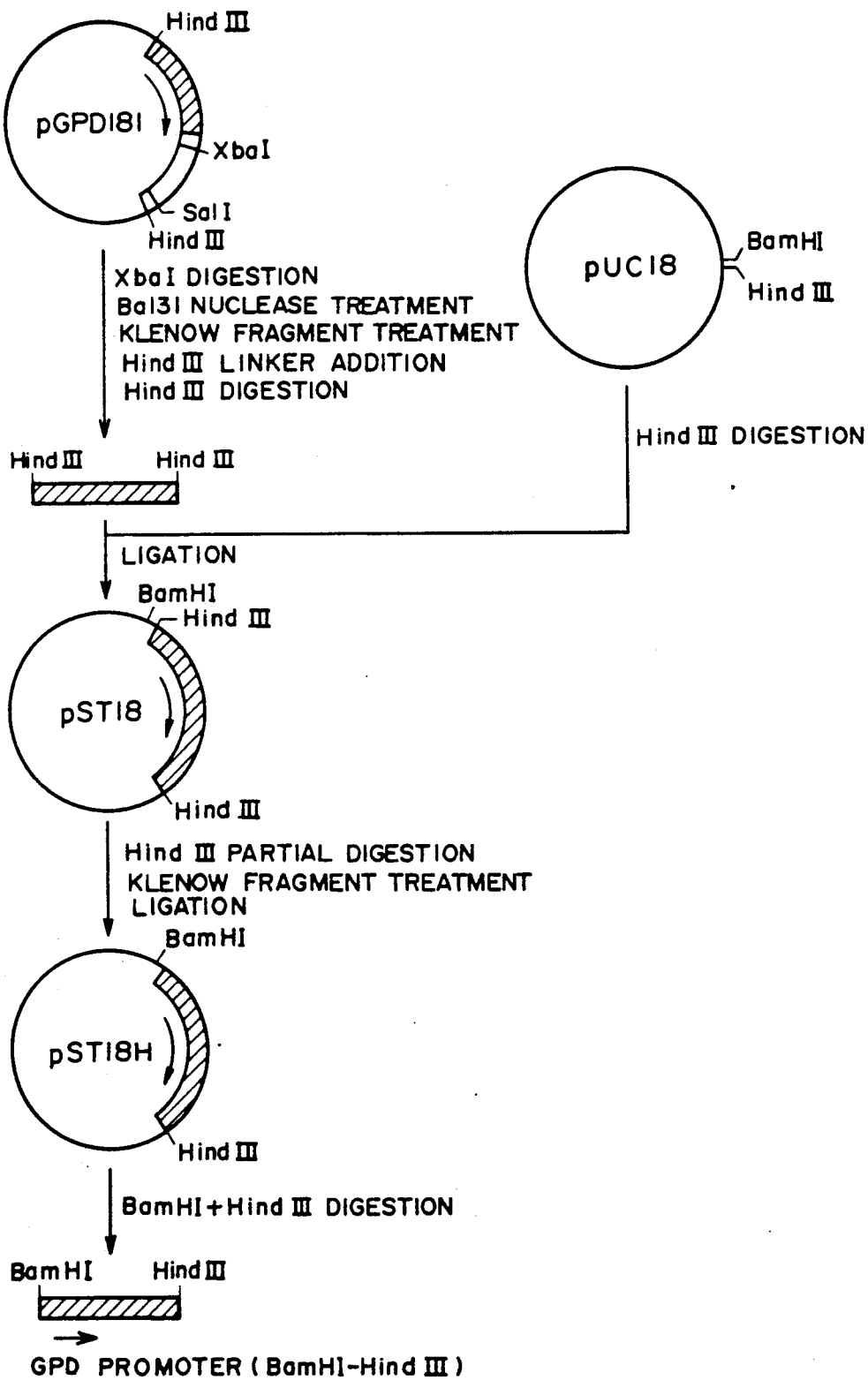
FIG. 8 is a flow chart for obtaining GPD promoter (BamHI-HindIII)

According to the method outlined in FIG. 8, GPD promoter (BamHI-HindIII) was acquired.

First, pGPD181 constructed in Example (2)-(i) was cleaved with XbaI, followed by Ba131 digestion to completely remove the coding region and treatment with Klenow fragment. To the blunt end was linked HindIII linker (Takara Shuzo, Japan), and the product was then digested with HindIII to excise the fragment containing the promoter region. The fragment was then inserted into the HindIII cleavage site of pUC18. The plasmid thus constructed is in two types in view of the orientation of the HindIII fragment inserted, and the plasmid in which the multiple cloning site which originated from pUC18 was located upstream from the GPD promoter was designated pST18. The pST18 was partially digested with HindIII, treated with Klenow fragment and re-ligated. Among the plasmids thus constructed, one which had the HindIII cleavage site upstream from the GPD promoter destroyed was designated plasmid pST18H. The fragment containing the GPD promoter, which was excised from the pST18 with BamHI and HindIII, was designated GPD promoter (BamHI-HindIII).

(v) Acquirement of PGK terminator

Figure 9:
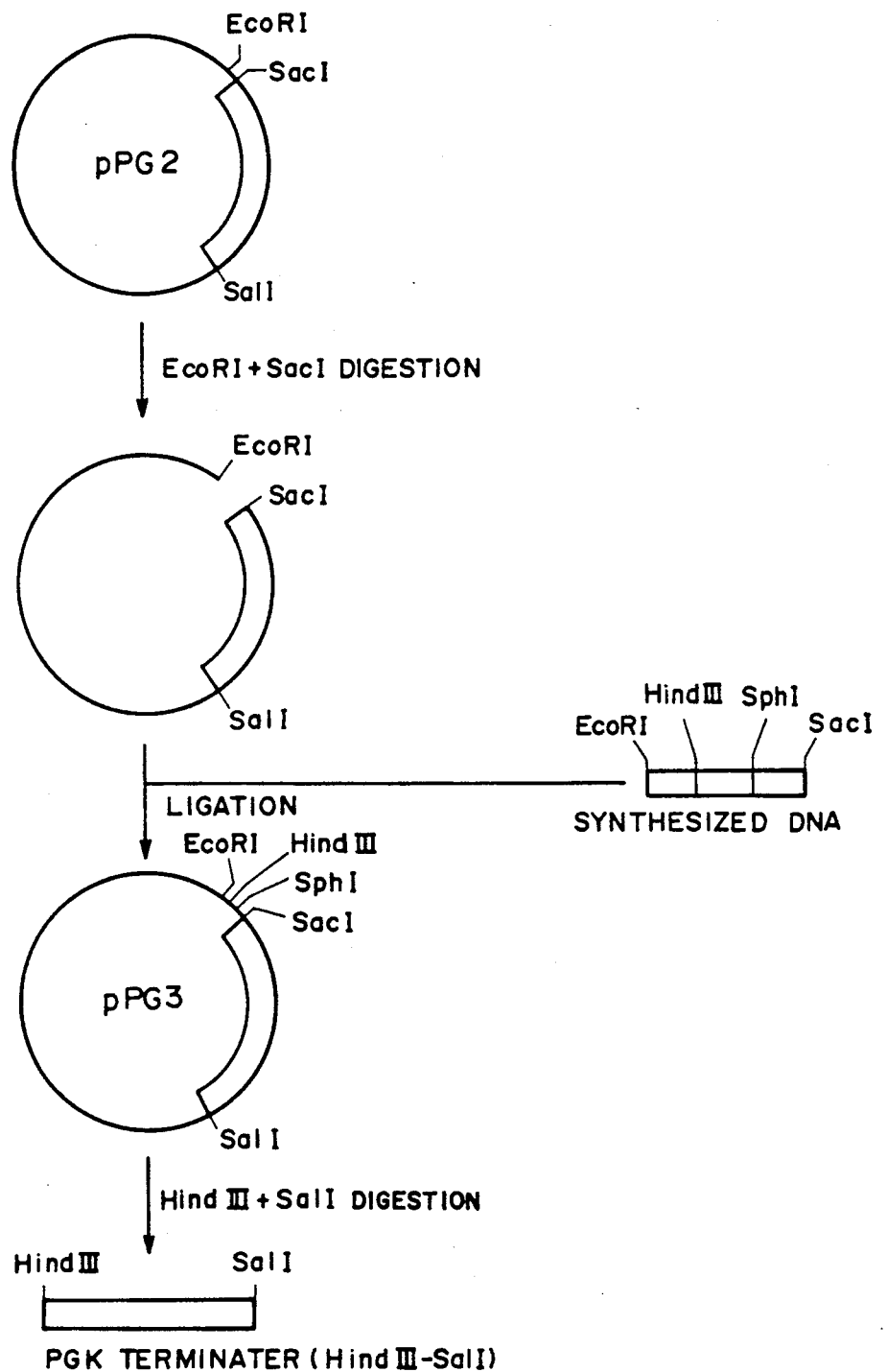
FIG. 9 is a flow chart for obtaining PGK terminator (Hind III-SalI)

According to the method outlined in FIG. 9, PGK

TABLE 2

| DNA | Nucleotide sequence | Plasmids constructed |
|---|---|---|
| F | HindIII  DraI                                    NcoI<br>⌐⌐  ⌋                                        ⌐<br>AGCTTTAAA<u>ATG</u>CGTCCGCGCATGAACCGCCTGTACCAGACATCGAC<br>          6<br>    AATTTTACGCAGGCGCGTACTTGGCGGACATGGTCTGTAGCTGGTAC | pALDC6 |
| G | HindIII  DraI                       NcoI<br>⌐⌐  ⌋                           ⌐<br>AGCTTTAAA<u>ATG</u>AACCGCCTGTACCAGACATCGAC<br>          7<br>    AATTTTACTTGGCGGACATGGTCTGTAGCTGGTAC | pALDC7 |

These synthesized DNAs have nucleotide sequences from either of the underlined portion 6 or 7 in FIG. 1 to the NcoI cleavage site, and have DraI cleavage site immediately upstream to the portion 6 or 7 underlined. These DNAs also have the cohesive ends of HindIII and NcoI. The DNA fragment from the HindIII site which originated from pUC19 to the NcoI site in the α-ALDCase gene was removed from pAX6. Then, the synthesized DNA, F or G, was ligated to the remnant part of pAX6. The resulting plasmids were designated pALDC6 and pALDC7, respectively. The fragments terminator (HindIII - SalI) was obtained.

First, the synthesized double stranded DNA of the following nucleotide sequence was inserted between EcoRI cleavage site and SacI cleavage site of pPG2 constructed in Example (2)-(ii) to construct plasmid pPG3, which synthesized double stranded DNA had HindIII and SphI cleavage sites and had cohesive ends of EcoRI and SacI.

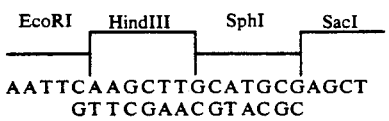

```
AATTCAAGCTTGCATGCAGCT
    GTTCGAACGTACGC
```

Figure 10:
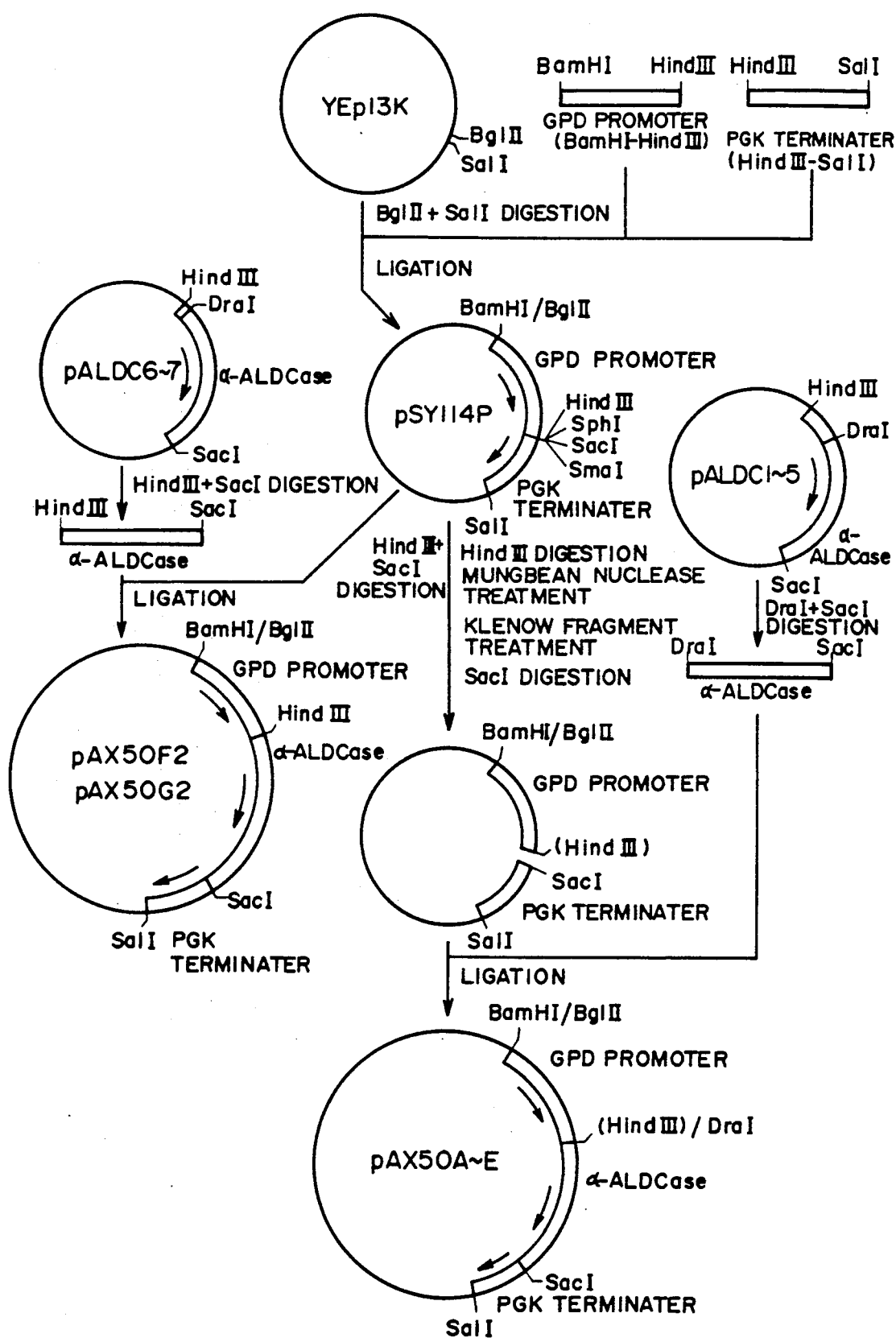
FIG. 10 is a flow chart for obtaining pAX50A to E.

Digestion of pPG3 with HindIII and SalI produced HindIII-SalI fragment containing pGK terminator region, which was designated PGK terminator (HindIII-SalI). (vi) Construction of expression plasmid:

The method used is outlined in FIG. 10.

First, the GPD promoter (BamHI-HindIII) obtained in Example (4)-(iv) and the PGK terminator (HindIII-SalI) obtained in Example (4)-(v) were inserted between the BglII cleavage site and SalI cleavage site in the plasmid YEP13K to construct plasmid pSY114P.

The plasmid pSY114P is capable of expressing a gene in yeast by means of the GPD promoter and the PGK terminator, which gene has been inserted in it in specified orientation between the HindIII cleavage site and SacI cleavage site. From each of pALDC1, pALDC2, pALDC3, pALDC4 and pALDC5, five DraI-SacI fragments containing the α-ALDCase gene were excised. pSY114P was digested with HindIII, and was then treated with mungbean nuclease (Takara Shuzo, Japan) thereby to remove the cohesive termini. The fragment obtained was then processed by Klenow fragment, followed by digestion with SacI. The fragment thus obtained was then ligated to each of the five DraI-SacI fragments containing the α-ALDCase gene as referred to hereinabove to construct five plasmids: pAX50A, pAX50B, pAX50C, pAX50D, and pAX50E. These plasmids respectively contain the α-ALDCase gene originated from pALDC1, pALDC2, pALDC3, pALDC4 and pALDC5 and capable of expressing the α-ALDCase gene in yeast.

On the other hand, the HindIII-SacI fragments containing the α-ALDCase were excised respectively from pALDC6 and pALDC7, and inserted between the HindIII cleavage site and the SacI cleavage site of pY114P to construct expression plasmids: pAX50F2 and pAX50G2. The pAX50F2 and pAX50G2 contain the u-ALDCase gene originated respectively from pALDC6 and pALDC7.

When α-ALDCase genes of above-mentioned expression plasmids were expressed in yeast, the translation start points and the polypeptides produced are assumed to be as follows.

| Expression plasmid | Translation initiation site | Polypeptide encoded |
|---|---|---|
| pAX50A | Portion 1 underlined in FIG. 1 | $A_1$ to B in FIG. 1 |
| pAX50B | Portion 2 underlined in FIG. 1 | $A_2$ to B in FIG. 1 |
| pAX50C | Portion 3*1 underlined in FIG. 1 | $A_3$ to B*2 in FIG. 1 |
| pAX50D | Portion 4 underlined in FIG. 1 | $A_4$ to B*2 in FIG. 1 |
| pAX50E | Portion 5*1 underlined in FIG. 1 | $A_5$ to B*2 in FIG. 1 |
| pAX50F2 | Portion 6*1 underlined in FIG. 1 | $A_6$ to B*2 in FIG. 1 |
| pAX50G2 | Portion 7 underlined in FIG. 1 | A to B in FIG. 1 |

*1 GTG has been converted into ATG
*2 Val in the N-terminus is replaced by Met (vii) Expression in yeast Laboratory yeast TD4 was transformed with the seven expression plasmids: pAX50A to E, pAX50F2 and pAX50G2, constructed in Example (4)-(vi).

The α-ALDCase activities of the transformants obtained were determined by the same method as in Example (2)-(iv).

The results obtained are set forth in the following Table, wherein it is shown that every transformant containing the expression plasmid exhibited α-ALDCase activity.

| Strain tested | Polypeptide encoded | α-ALDCase activity (U/mg-protein) |
|---|---|---|
| TD4 + YEp13K | — | 0 |
| TD4 + pAX50A | $A_1$ to B in FIG. 1 | 2.7 |
| TD4 + pAX50B | $A_2$ to B in FIG. 1 | 6.9 |
| TD4 + pAX50C | $A_3$ to B* in FIG. 1 | 18.0 |
| TD4 + pAX50D | $A_4$ to B in FIG. 1 | 21.2 |
| TD4 + pAX50E | $A_5$ to B* in FIG. 1 | 35.2 |
| TD4 + pAX50F2 | $A_6$ to B* in FIG. 1 | 17.0 |
| TD4 + pAX50G2 | A to B in FIG. 1 | 35.8 |

*Val at the N-terminus is replaced by Met.

Figure 11:
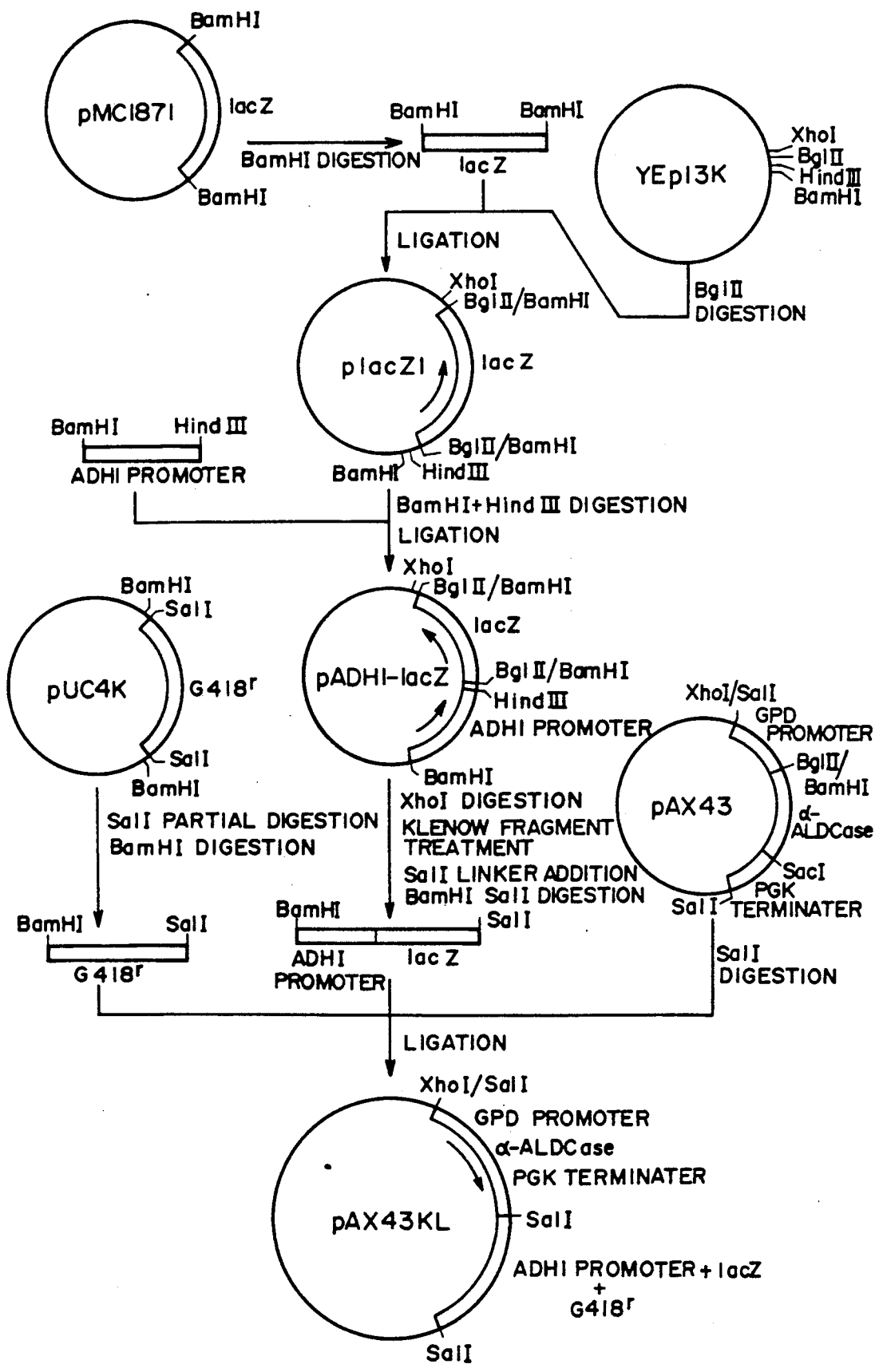
FIG. 11 is a flow chart for constructing pAX43KL.

(5) Confirmation in fermentation test of reduction in diacetyl formation (i) Construction of an expression vector for beer yeast, pAX43KL The method used is outlined in FIG. 11.

First, ADH1 promoter + lacZ gene which is capable of expressing β-galactosidase in yeast was obtained as follows. Thus, lacZ gene (E. coli β-galactosidase gene) was obtained as a BamHI fragment from plasmid pMC1871 (Pharmacia). This fragment (lacZ gene) lacks the promoter and translation start points. This fragment was inserted into BglII site of plasmid YEp13K in the direction indicated by the arrow in FIG. 11 to construct the plasmid placZ1. The lacZ gene in placZ acquired the new translation start codon (ATG) which located in the same reading frame as lacZ between BglII and HindIII sites originated in YEp13K. The ADH1 promoter obtained in Example (3)-(i) was inserted between BamHI and HindIII sites of placZ1 to construct the plasmid pADH1-lacZ in which the ADH1 promoter was used to express lacZ. The pADH1-lacZ was digested with XhoI, and was then processed It was confirmed that TDA concentration in wort fermented by YAL3-1 or YAL3-2 was significantly lower than that in wort fermented by the control strain.

| Yeast tested | Apparent*1 attenuation | TDA*2 (mg/lit) |
|---|---|---|
| Beer yeast (1) | 72.6 | 0.99 |
| Beer yeast (2) | 72.6 | 1.00 |
| Average | 72.6 | 1.00 |
| Beer yeast + pAX43XL (1) (YAL3-1) | 72.3 | 0.28 |
| Beer yeast + pAX43XL (2) (YAL3-1) | 72.3 | 0.33 |
| Average | 72.3 | 0.31 |
| Beer yeast + pAX43XL (1) (YAL3-2) | 75.4 | 0.32 |
| Beer yeast + pAX43XL (2) (YAL3-2) | 75.4 | 0.26 |

| Yeast tested | Apparent*1 attenuation | TDA*2 (mg/lit) |
| --- | --- | --- |
| Average | 75.4 | 0.29 |

*1 Apparent attenuation is defined as follows. Apparent attenuation (%) = [Original wort extract (°P) - apparent extract of the fermented wort (°P)] × 100/[Original wort extract (°P)]
*2 TDA comprises vicinal diketones and acetohydroxylic acid (mainly DA and its precursor, i.e. α-AL).

(6) Introduction of the α-ALCDase gene into yeast (Part 4)

Integration of the α-ALDCase gene into a yeast chromosome, expression and fermentation test

Figure 12:
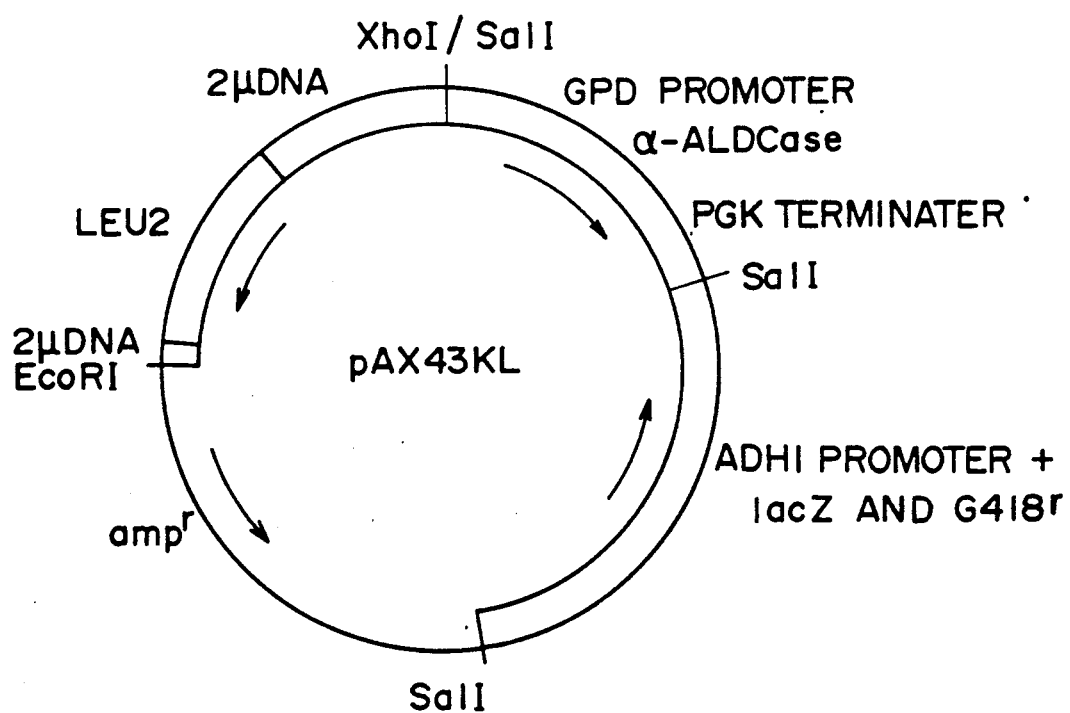
FIG. 12 illustrate the structure of pAX43KL.

(i) Outline of the method of integrating the α-ALDCase gene into the yeast chromosome The α-ALDCase gene which had been capable of expression in yeast by the addition of the GPD promoter with Klenow fragment, followed by addition of SalI linker (Takara Shuzo, Japan). From the fragment ADHl promoter +lacZ gene was then excised as a BamHI-SalI fragment. G418 resistant gene, on the other hand, was excised from pUC4K (Pharmacia) as a SalI-BamHI fragment by partial digestion with SalI and complete digestion with BamHI. This fragment containing the G418 resistant gene and the BamHI-SalI fragment containing ADHl promoter +lacZ gene referred to above were inserted into the SalI cleavage site of pAX43 constructed in Example (2)-(iii) to construct plasmid pAX43KL (FIG. 12).

(ii) Introduction of pAX43KL into beer yeast

A conventional beer yeast was transformed with the pAX43KL according to the lithium acetate method. The G418-resistant colonies having β-galactosidase activity were selected as the real transformants. These transformants exhibited the α-ALDCase activity of 3.2 to 7.0 U/mg protein. Two independent strains among the transformants were respectively designated YAL3-1 and YAL3-2.

(iii) Fermentation test

YAL3-1 and YAL3-2 obtained in Example (ii) were cultured statically in 50 ml of wort containing 10 ppm of G418 at 20° C. for 3 days. The whole cultures were added to 1 liter of wort containing 10 ppm of G418, and further cultured statically at 8° C. for 10 days. Then, cells were collected by centrifugation (5000 rpm, 10 min.). The cells obtained were used to inoculate wort of 11° P. (plato) at inoculum level of 0.5% (0.5 g wet cells/100 ml wort). After sufficient aeration, fermentation was conducted at 8° C. for 8 days. After completion of fermentation, cells were removed by centrifugation and filtration with a filter paper. Then, the amount of TDA (total diacetyl) and apparent attenuation degree of the fermented wort were determined.

Figure 13:
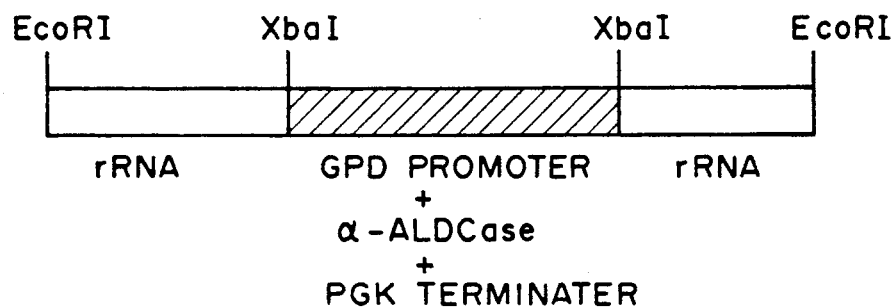
FIG. 13 illustrates the structure of a DNA fragment containing GPD promoter+α-ALDCase gene+PGK terminator.

The results obtained are set forth in the following Table. and the PGK terminator was inserted into the yeast rRNA gene to prepare a fragment illustrated in FIG. 13. This fragment was transformed together with a YEp type plasmid carrying the G418 resistant gene into yeast, and the G418-resistant transformants were selected. Among these transformants, a transformant such that the aforementioned α-ALDCase gene had been integrated into the rRNA gene of the yeast chromosome by homologous recombination was successfully obtained.

(ii) Construction of the integration type plasmid (pAX60G2)

Figure 15:
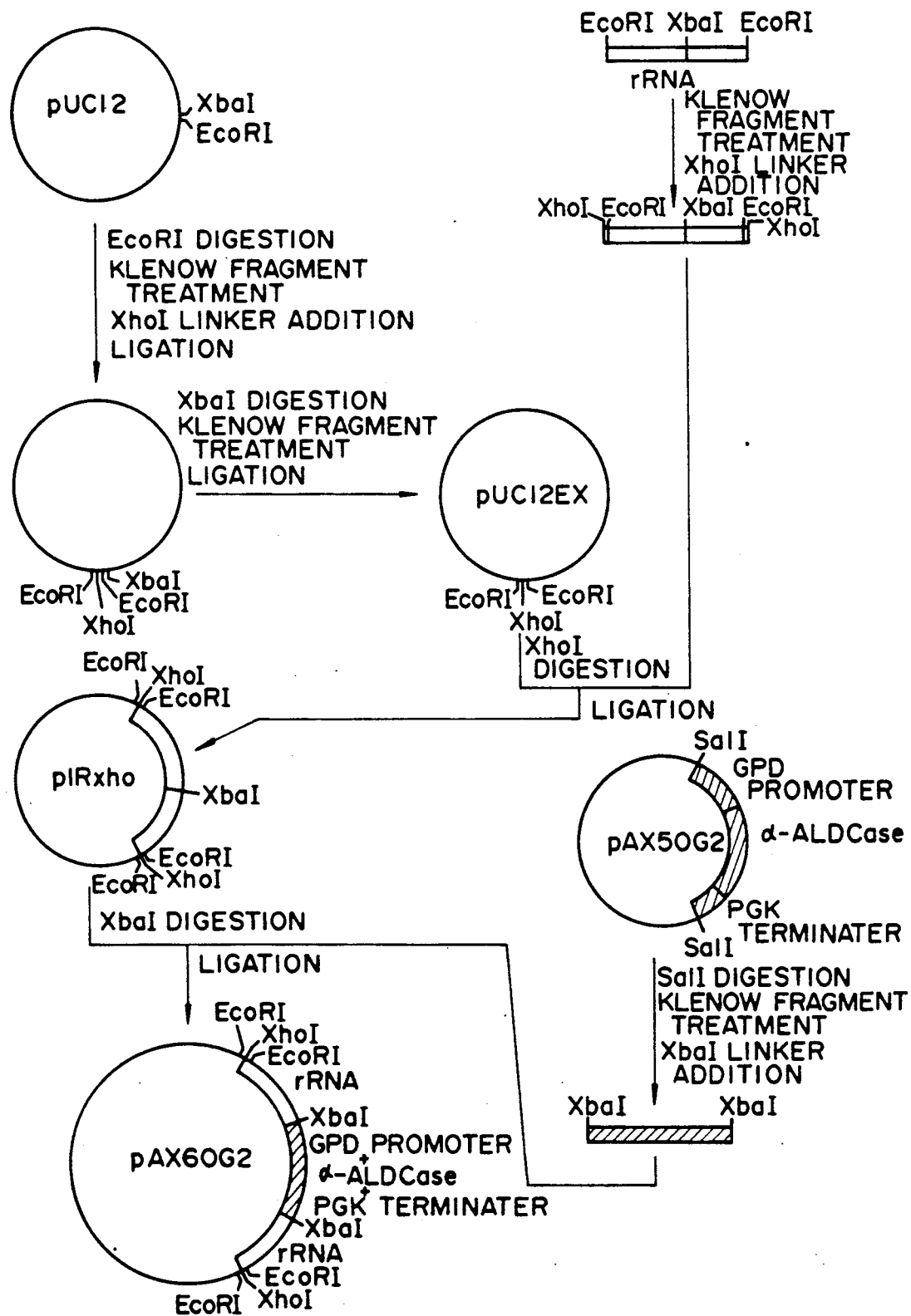
FIG. 15 is a flow chart for constructing pAX60G2.

Plassmid pAX60G2 which has no replication origin in yeast and can be carried on yeast only when it is integrated into the chromosome (of the yeast) was constructed according to the method illustrated schematically in FIG. 15.

First, the EcoRI cleavage site of plasmid pUC12 (Pharmacia) was treated with Klenow fragment, and XhoI linkers (Takara Shuzo) were further added. Then, the plasmid was subjected again to ligation. This plasmid possesses a new XhoI cleavage site, and in the same time the EcoRI cleavage sites regenerated at the both sides of the XhoI cleavage site. This plasmid was cleaved with XbaI, treated with a Klenow fragment and then subjected to ligation again. The plasmid pUC12EX thus obtained contains no XbaI cleavage site.

An oligonucleotide was synthesized which corresponded to the nucleotide sequence from position 4 to position 32 at the 5'-terminal region of a 5.8S rRNA gene [J. Biol. Chem. 252, 8118–8125 (1977)]. After being labelled with $^{32}P$ at the 5'-terminus, this was used as a probe to isolate rRNA genes from the library prepared in Example (2)-(i).

A 3 kb EcORI fragment was excised from the isolated rRNA genes. This fragment contained a part of the 5.8S rRNA gene and a part of the 2.8S rRNA gene. This fragment was treated with Klenow fragment before addition of XhoI linkers. The fragment was then inserted into the XhoI site of the plasmid pUC12EX.

Moreover, plasmid pAX50G2 constructed in (4)-(vi) was cleaved with SalI, and a fragment containing the GPD promoter, the α-ALDCase gene and the PGK promoter (this fragment is illustrated by the hatched box in FIG. 15) was obtained. The fragment was treated with Klenow fragment, followed by ligation to XbaI linker (Pharmacia). Then, the XbaI fragment was inserted into the XbaI cleavage site of the pIR$_{xho}$ to construct plasmid pAX60G2.

Figure 16:
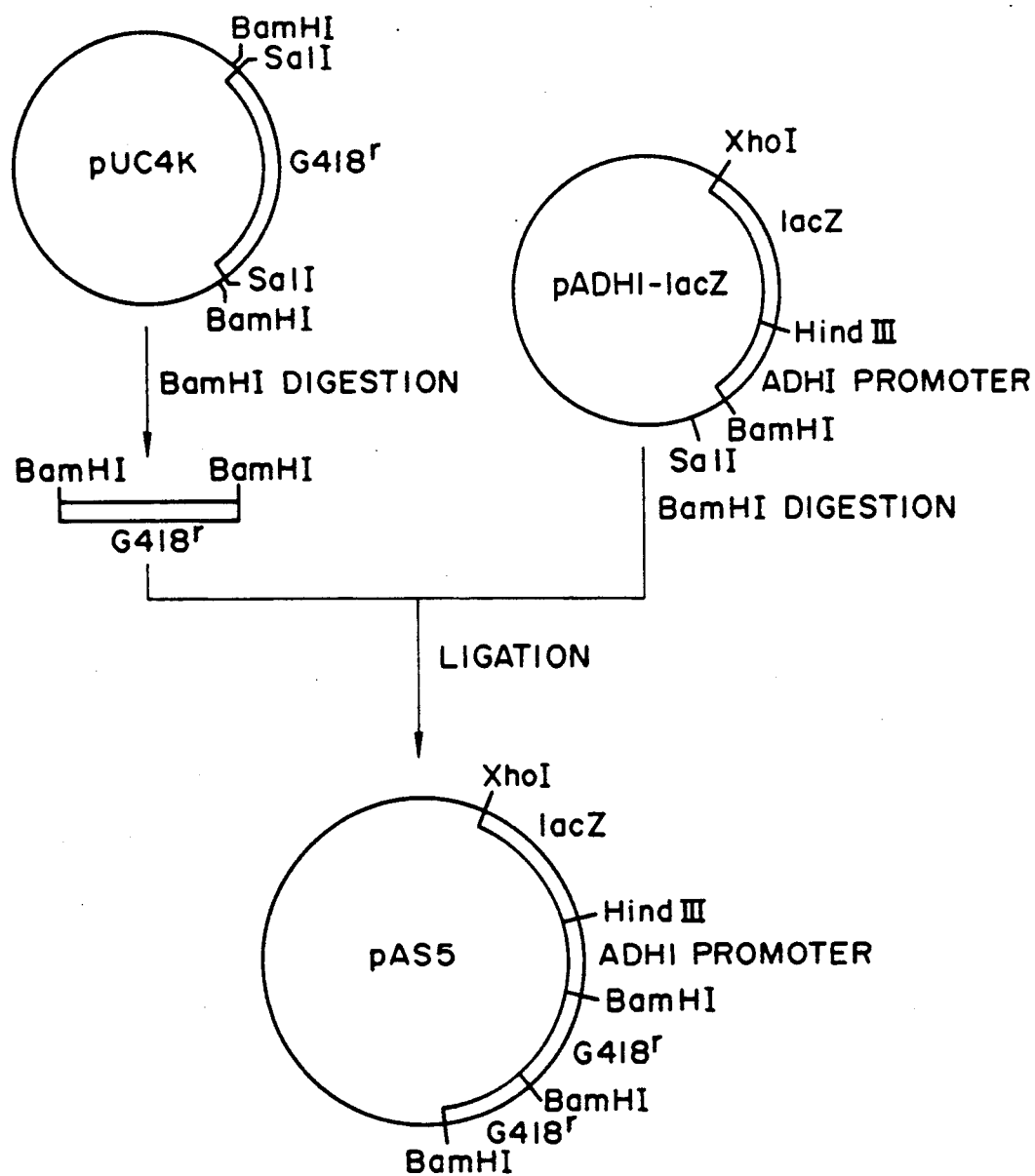
FIG. 16 is a flow chart for constructing pAS5.

(iii) Construction of YEp type plasmid pAS5 containing the G418 resistant gene Plasmid pAS5 was constructed according to the method illustrated schematically in FIG. 16.

First, the fragment containing the G418-resistant gene (G418r) was excised with BamHI from the plasmid pUC4K (Pharmacia) and inserted into the BamHI cleavage site of pADHl-lacZ obtained in (5)-(i). Among the plasmids thus obtained, one into which two G418 resistant genes had been inserted was designated pAS5. The degree of resistance to G418 was greater when the plasmid pAS5 was used for transformation than when a plasmid containing one G418, gene was used.

Figure 14:
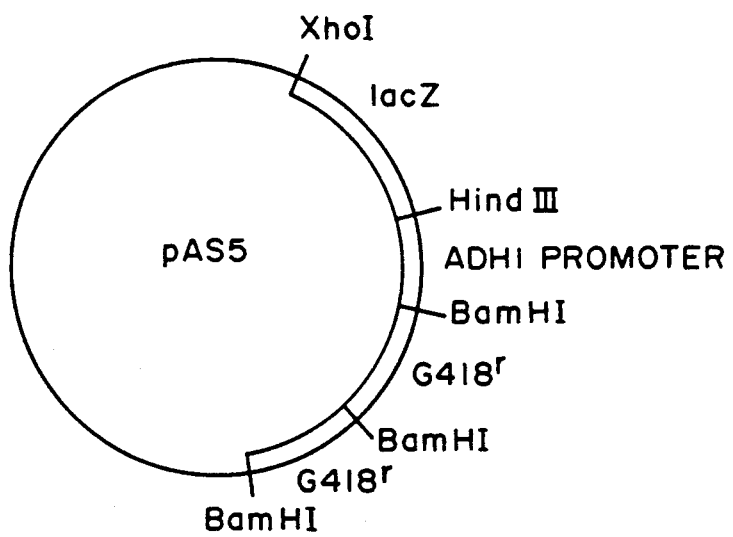
FIG. 14 illustrates the structure of pAS5.

(iv) Integration of the α-ALDCase gene into a yeast chromosome DNA:

Beer yeast IFO 0751 was co-transformed by the lithium acetate method with the fragment which was obtained by the EcoRI digestion of pAX6uG2 obtained in (ii) (i.e. the fragment in FIG. 13) and pAS5 obtained in (iii) (FIG. 14). G418 resistance and β-galactosidase activity were used as markers to select transformants. A transformant thus obtained was cultured aerobically in YPD medium at 30° C. overnight, and then strains having the α-ALDCase gene were obtained by measuring the α-ALDC activity. These strains were subcultured non-selectively for 12-13 generations in YPD medium, and then the appropriately diluted cultures were respectively plated on Ruby's agar media containing X-gal (5'-bromo-4'-chloro-3'-indolyl-β-D-galactoside) [Method in Enzymology, vol, 101, 253 (1983)]. These plates were incubated at 30° C. for 3-5 days, and colonies not exhibiting blue color that is, strains showing no β-galactosidase activity were obtained. It is believed that these strains do not have PAS5, but have only the α-ALDCase expression unit integrated into chromosome DNA which consists of the GPD promoter, the α-ALDCase gene and the PGK terminator. These strains had been cultured aerobically in the YPD medium at 30° C. overnight, and then the α-ALDCase activity was measured. Among these strains, one which exhibits ALDCase activity of 1.0 U/mg protein is designated YAL4. When YAL4 was subcultured for 47 generations in YPD medium, the α-ALDCase activity was maintained at a level of 75% or more.

(v) Fermentation test

The YAL4 obtained in (iv) was cultured statically in 50 ml of wort at 20° C. for 3 days, and the whole culture was used to inoculate 1 liter of wort to continue static culture at 10° C. for 10 days. Yeast cells thus grown up were collected by centrifugation (5,000 rpm × 10 min). The yeast cells thus obtained were used to inoculate wort of 11° P. at inoculum level of 0.6% (wet W/V). This culture was aerated sufficiently by stirring, and then static fermentation was conducted at 10° C. for 10 days. After completion of fermentation, the yeast cells were removed by centrifugation and filtration with a filter paper, and the amount of TDA (total diacetyl) and apparent attenuation degree of the fermented wort were measured. Results are shown in the following table. It was found that the amount of TDA was decreased in the fermentation with the yeast of the present invention as compared with a fermentation with a control strain.

| Strain | | Apparent attenuation degree | TDA (mg/lit) |
|---|---|---|---|
| IF00751 | 1 | 74.4 | 0.95 |
| | 2 | 72.8 | 1.04 |
| | Average | 73.6 | 1.00 |
| YAL4 | 1 | 73.8 | 0.46 |
| | 2 | 71.7 | 0.50 |
| | Average | 72.8 | 0.48 |

Deposition of microorganism

The strain YAL2 was deposited at Fermentation Research Institute, Agency of Industrial Science and Technology at 1-3, Higashi 1 chome, Yatabe-machi, Tsukuba-gun, Ibaraki-ken, 305, Japan on Apr. 7, 198 under an accession number of FERM BP-1844.

The plasmid pAX6 containing the DNA fragment in accordance with the present invention was deposited as E. coli JM109 (containing pAX6), which is E. coli JM109 (Takara Shuzo, Japan) harboring the pAX6, at the Fermentation Research Institute on Dec. 14, 1988 under an accession number of FERM BP-2187.

The strain YAL4 was deposited at the Fermentation Research Institute on Apr. 7, 1989 under an accession number of FERM BP-2374.

These deposits are under the Budapest Treaty on the international recognition of the deposit of microorganisms for the purpose of patent procedure.

What is claimed is:

1. An isolated DNA sequence which comprises a nucleotide sequence coding for a polypeptide having α-acetolactate decarboxylase activity, the polypeptide having an amino acid sequence which comprises from A to B of the amino acid sequence shown in FIG. 1.

2. A DNA sequence of claim 1, which has a nucleotide sequence of from A to B of the nucleotide sequence shown in FIG. 1 or its degenerative isomer.

3. A yeast belonging to the species Saccharomyces cerevisiae having reduced α-acetolactate producing ability, which has been transformed with a DNA sequence which comprises a nucleotide sequence coding for a polypeptide having α-acetolactate decarboxylase activity, the polypeptide having an amino acid sequence which comprises from A to B of the amino acid sequence shown in FIG. 1.

4. A yeast according to claim 3, wherein the nucleotide sequence is in the form of a plasmid containing the same.

5. A yeast according to claim 3, wherein the DNA sequence has the nucleotide sequence of from A to B of the nucleotide sequence shown in FIG. 1.

6. A process for producing a yeast having reduced α-acetolactate producing ability, which process comprises transforming a host yeast belonging to the species Saccharomyces cerevisiae with a DNA sequence which comprises a nucleotide sequence coding for a polypeptide having α-acetolactate decarboxylase activity, the polypeptide having an amino acid sequence which comprises from A to B of the amino acid sequence shown in FIG. 1.

7. A process for producing a yeast having reduced α-acetolactate producing ability as claimed in claim 6, wherein the nucleotide sequence is one from A to B of the nucleotide sequence shown in FIG. 1 or its degenerative isomer.

8. A process for producing a yeast having reduced α-acetolactate producing ability as claimed in claim 6, wherein the nucleotide sequence is in the form of a plasmid containing the same.

9. A process for producing a yeast having reduced α-acetolactate producing ability as claimed in claim 7, wherein the DNA sequence has the nucleotide sequence of from A to B of the nucleotide sequence shown in FIG. 1.

10. In a process for producing an alcoholic beverage by fermentation wherein a yeast is caused to act upon a substrate to produce ethanol at a temperature conducive to said fermentation, the improvement which comprises the use of a yeast belonging to the species Saccharomyces cerevisiae having reduced α-acetolactate producing ability, which yeast has been transformed with a DNA sequence which comprises a nucleotide sequence coding for a polypeptide having α-acetolactate decarboxylase activity, the polypeptide having an amino acid sequence which comprises from A to B of the amino acid sequence shown in FIG. 1.

11. The process for producing an alcoholic beverage as claimed in claim 10, wherein the nucleotide sequence is in the form of a plasmid containing the same.

12. The process for producing an alcohol beverage as claimed in claim 10, wherein the DNA sequence comprises the nucleotide sequence of from A to B of the nucleotide sequence shown in FIG. 1.

13. The process for producing an alcohol beverage as claimed in claim 10, wherein the alcoholic beverage is beer.

14. A recombinant DNA vector having a DNA sequence which has a nucleotide sequence coding for a polypeptide having α-acetolactate decarboxylase activity, the polypeptide having an amino acid sequence which comprises from A to B of the amino acid sequence shown in FIG. 1, said vector being effective for use in transforming a yeast which is suitable for causing fermentation at certain temperatures, said yeast belonging to the species Saccharomyces cerevisiae, said vector being effective in transforming said yeast such that the yeast so transformed has the ability to produce α-acetolactate decarboxylase without substantial impairment of its effectiveness to cause said fermentation at said temperatures.

15. An isolated DNA sequence of claim 1, wherein the amino acid sequence of said polypeptide is from A to B or from $A_5$ to B of the nucleotide sequence shown in FIG. 1.

16. The process for producing an alcoholic beverage as claimed in claim 10, wherein the amino acid sequence of said polypeptide is from A to B or from $A_5$ to B of the nucleotide sequence shown in FIG. 1.

17. A process as claimed in claim 10 wherein the yeast has been transformed with said DNA sequence without substantially impairing the effectiveness of the yeast to cause said fermentation at said temperature.

18. A process as claimed in claim 13 wherein said yeast which has been transformed is effective to cause said fermentation at about 10° C.

19. A process as claimed in claim 6 wherein prior to said transformation the host yeast is effective to cause fermentation of a substrate at certain temperatures, and wherein said transformation endows said yeast with the ability to produce α-acetolactate decarboxylase without substantially impairing its effectiveness to cause said fermentation at said temperatures.

20. A yeast as claimed in claim 3 wherein prior to having been transformed said yeast is effective to cause fermentation of a substrate at certain temperatures, and wherein after having been transformed said yeast has the ability to produce α-acetolactate decarboxylase without substantial impairment of its effectiveness to cause said fermentation at said temperatures.

* * * * *